United States Patent
Steidl et al.

(10) Patent No.: US 9,873,918 B2
(45) Date of Patent: Jan. 23, 2018

(54) TREATMENT OF ACUTE MYELOID LEUKEMIA AND MYELODYSPLASTIC SYNDROMES

(75) Inventors: Ulrich G. Steidl, New Rochelle, NY (US); Laura Barreyro De Pujato, Bronx, NY (US); Britta Will, Bronx, NY (US); Amit Verma, Bronxville, NY (US)

(73) Assignee: Albert Einstein College of Medicine, Inc., Bronx, NY (US)

(*) Notice: Subject to any disclaimer, the term of this patent is extended or adjusted under 35 U.S.C. 154(b) by 153 days.

(21) Appl. No.: 14/236,118

(22) PCT Filed: Aug. 9, 2012

(86) PCT No.: PCT/US2012/050062
§ 371 (c)(1),
(2), (4) Date: Mar. 26, 2014

(87) PCT Pub. No.: WO2013/023015
PCT Pub. Date: Feb. 14, 2013

(65) Prior Publication Data
US 2015/0147271 A1    May 28, 2015

Related U.S. Application Data

(60) Provisional application No. 61/522,353, filed on Aug. 11, 2011.

(51) Int. Cl.
    A61K 39/00     (2006.01)
    C07K 14/54     (2006.01)
    C07K 16/24     (2006.01)
    C12Q 1/68      (2006.01)
    A61K 39/395    (2006.01)
    A61K 31/7088   (2006.01)
    A61K 35/15     (2015.01)
    A61K 47/48     (2006.01)
    A61K 51/10     (2006.01)
    G01N 33/68     (2006.01)

(52) U.S. Cl.
    CPC ........ C12Q 1/6886 (2013.01); A61K 31/7088 (2013.01); A61K 35/15 (2013.01); A61K 39/395 (2013.01); A61K 47/48538 (2013.01); A61K 47/48546 (2013.01); A61K 47/48561 (2013.01); A61K 51/1018 (2013.01); A61K 51/1021 (2013.01); A61K 51/1027 (2013.01); A61K 51/1033 (2013.01); C07K 16/244 (2013.01); G01N 33/6869 (2013.01); A61K 2039/505 (2013.01); C07K 14/5421 (2013.01); C12Q 2600/112 (2013.01); C12Q 2600/118 (2013.01); C12Q 2600/158 (2013.01); C12Q 2600/16 (2013.01); G01N 2333/7155 (2013.01); G01N 2333/914 (2013.01); G01N 2500/10 (2013.01)

(58) Field of Classification Search
    CPC .. C07K 16/00; C07K 16/244; C07K 14/5421; A61K 2039/505; A61K 39/395
    See application file for complete search history.

(56) References Cited

U.S. PATENT DOCUMENTS

| | | | |
|---|---|---|---|
| 7,723,112 | B2 | 5/2010 | Clarke et al. |
| 7,939,263 | B2 | 5/2011 | Clarke et al. |
| 8,361,736 | B2 | 1/2013 | Majeti et al. |
| 8,562,997 | B2 | 10/2013 | Jaiswal et al. |
| 2005/0202451 | A1 | 9/2005 | Burczynski et al. |
| 2007/0198198 | A1 | 8/2007 | Burczynski et al. |
| 2008/0280774 | A1 | 11/2008 | Burczynski et al. |
| 2009/0191164 | A1 | 7/2009 | Majeti et al. |
| 2009/0191202 | A1 | 7/2009 | Jamieson et al. |
| 2011/0059852 | A1 | 3/2011 | Karsunky |
| 2011/0183866 | A1 | 7/2011 | Clarke et al. |
| 2012/0225059 | A1 | 9/2012 | Fioretos et al. |
| 2012/0282174 | A1 | 11/2012 | Weissman et al. |
| 2013/0142786 | A1 | 6/2013 | Liu et al. |
| 2013/0216558 | A1 | 8/2013 | Karsunky |
| 2013/0244326 | A1 | 9/2013 | Majeti et al. |
| 2014/0017167 | A1 | 1/2014 | Fioretos et al. |
| 2014/0030786 | A1 | 1/2014 | Clarke et al. |

FOREIGN PATENT DOCUMENTS

WO    2011021014 A2    2/2011

OTHER PUBLICATIONS

Gura, T. Systems for identifying new drugs are often faulty. Science, 1997, vol. 278, p. 1041-1042.*
Hartfield, K.J. et al. Antiangiogenic therapy in acute myelogenous leukemia: Targeting of vascular endothelial growth factor and interleukin 8 as possible antileukemic strategies. Current Cancer Drug Targets, 2005, vol. 5, p. 229-248.*
Communication in Cases for Which No Other Form Is Applicable dated Jun. 12, 2013 from the International Bureau in connection with PCT International Patent Application No. PCT/US2012/050062, 2 pages.
PCT International Search Report and Written Opinion, dated Jan. 22, 2013 in connection with PCT International Application No. PCT/2012/50062, 12 pages.
Rosen JM et al., entitled "The increasing complexity of the cancer stem cell paradigm," Science, Jun. 26, 2009; vol. 324, No. 5935, pp. 1670-1673.
Barreyro L et al., entitled "Overexpression of IL-1 receptor accessory protein in stem and progenitor cells and outcome correlation in AML and MDS," Blood; ePub Jun. 21, 2013; vol. 120, 6, pp. 1290-1298.
Jaras M et al., Isolation and killing of candidate chronic myeloid leukemia stem cells by antibody targeting of IL-1 receptor accessory protein. Proc. Nat'l. Acad. Sci. 107 (37): 16280-16285, Sep. 14, 2010.
Numomura K et al., Cell surface labeling and mass spectrometry reveal diversity of cell surface markers and signaling molecules expressed in undifferentiated mouse embryonic stem cells. Mol. & Cell. Proteomics 4: 1968-1976, 2005.

(Continued)

Primary Examiner — Robert Landsman
Assistant Examiner — Bruce D Hissong
(74) Attorney, Agent, or Firm — Amster, Rothstein & Ebenstein LLP

(57) ABSTRACT

Methods are disclosed for diagnosis, prognosis and therapy of acute myeloid leukemia and myelodysplastic syndromes using interleukin 1 receptor accessory protein and other targets.

10 Claims, 21 Drawing Sheets

(56) References Cited

OTHER PUBLICATIONS

Askmyr M et al., Selective killing of candidate AML stem cells by antibody targeting of IL1RAP. Blood Epub Mar. 11, 2013, 121(18): 3709-13, 2013.

Huang S et al., entitled "Fully Humanized Neutralizing Antibodies to Interleukin-8 (ABX-IL8) Inhibit Angiogenesis, Tumor Growth, and Metastasis of Human Melanoma," American Journal of Pathology, vol. 161, No. 1, Jul. 2002, pp. 125-134.

Mian B M et al., entitled "Fully Human Anti-Interleukin 8 Antibody Inhibits Tumor Growth in Orthotopic Bladder Cancer Xenografts via Down-Regulation of Matrix Metalloproteases and Nuclear Factor-κB1," Clinical Cancer Research, vol. 9, 3167-3175, Aug. 1, 2003.

Schinke C et al., entitled "IL8-CXCR2 pathway inhibition as a therapeutic strategy against MDS and AML stem cells," Blood, May 14, 2015, vol. 125, No. 20, pp. 3144-3152.

\* cited by examiner

SEQUENCE LISTING

<160> NUMBER OF SEQ ID NOS: 5

<210> SEQ ID NO 1
<211> LENGTH: 20
<212> TYPE: DNA
<213> ORGANISM: artificial
<220> FEATURE:
<223> OTHER INFORMATION: forward primer for IL-1RAP

<400> SEQUENCE: 1
tgcatctttg accgagacag        20

<210> SEQ ID NO 2
<211> LENGTH: 19
<212> TYPE: DNA
<213> ORGANISM: artificial
<220> FEATURE:
<223> OTHER INFORMATION: reverse primer for IL-1RAP

<400> SEQUENCE: 2
cggctgaaaa tgcagaaaa        19

<210> SEQ ID NO 3
<211> LENGTH: 26
<212> TYPE: DNA
<213> ORGANISM: artificial
<220> FEATURE:
<223> OTHER INFORMATION: Luciferase Control shRNA

<400> SEQUENCE: 3
gtgcgttgtt agtactaatc ctattt        26

<210> SEQ ID NO 4
<211> LENGTH: 29
<212> TYPE: DNA
<213> ORGANISM: artificial
<220> FEATURE:
<223> OTHER INFORMATION: IL-1RAP shRNA 1

<400> SEQUENCE: 4
tggccttact ctgatctggt attggacta        29

<210> SEQ ID NO 5
<211> LENGTH: 29
<212> TYPE: DNA
<213> ORGANISM: artificial
<220> FEATURE:
<223> OTHER INFORMATION: IL-1RAP shRNA 2

<400> SEQUENCE: 5
cgggcattaa ttgatttcct actatattc        29

TREATMENT OF ACUTE MYELOID LEUKEMIA AND MYELODYSPLASTIC SYNDROMES

CROSS-REFERENCE TO RELATED APPLICATIONS

This application is a U.S. national stage entry under 35 U.S.C. §371 of PCT International Patent Application No. PCT/US2012/50062, filed Aug. 9, 2012, which claims priority to U.S. Provisional Patent Application No. 61/522,353, filed Aug. 11, 2011, the contents of which are incorporated herein by reference into the subject application.

STATEMENT OF GOVERNMENT SUPPORT

This invention was made with government support under grant number CA131503 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Acute myeloid leukemia (AML) and myelodysplastic syndromes (MDS) are heterogeneous clonal neoplastic diseases that originate from transformed cells that have progressively acquired critical genetic changes that disrupt key differentiation- and growth-regulatory pathways (1). Recent experimental evidence suggests that AML and MDS originate from early hematopoietic stem cells (HSC) following the acquisition of multiple genetic or epigenetic changes that initially give rise to pre-leukemic HSC (pre-LSC) and then to fully transformed leukemia stem cells (LSC). Relapse continues to be the major cause of death in most subtypes of AML, suggesting that current therapies are largely ineffective in eliminating LSC and pre-LSC. As a consequence, future treatments should not only aim at reducing the bulk tumor (blast) population but must be directed against pre-LSC and LSC if one aims at a cure of the disease (3-5). Thus, defining the characteristics of pre-LSC and LSC, and of the earliest leukemia cells-of-origin (LCO) (defined as the earliest cells with clonotypic aberrations that lead to formation of pre-LSC and then LSC) is critical to understand the genesis of leukemia and to develop strategies by which these cells can be eradicated. However, the molecular mechanisms by which genetic and epigenetic events contribute to the formation and function of LCO and LSC are largely unknown. In the past, research efforts have focused on the bulk tumor cells, but this approach is hampered by at least two conceptual challenges. First, the bulk tumor cells appear at the final stage of disease and are hence likely to show many secondary alterations besides the primary oncogenic events that lead to cancer stem cell formation. Second, an adequate cellular control population is not available. This is particularly true for AML and MDS, in which a developmental block and/or dysplastic cells are hallmarks of the disease and result in a bulk tumor population of immature cells that cannot be easily compared to normal blood or bone marrow (BM) cells. In addition, the recent observation that LSC are contained within different phenotypic cellular compartments is a challenge for the identification of pathways contributing to the initiation and maintenance of AML. In order to address the problem of cellular heterogeneity within the tumor and to identify relevant pre-LSC and LSC pathways, novel experimental approaches other than the examination of bulk tumor cells need to be established. Transcriptional analysis is a potentially powerful method to reveal deregulated transcriptional networks and their effect on the function of normal and malignant HSCs and progenitors, particularly as genes encoding transcription factors, which govern these networks, are frequently mutated, rearranged, or otherwise disrupted in human AML and MDS (6-8).

The present invention addresses the need for markers and therapeutic targets in acute myeloid leukemia and myelodysplastic syndromes.

SUMMARY OF THE INVENTION

The present invention provides methods for determining the prognosis of a subject having acute myeloid leukemia (AML) comprising determining the level of expression of Interleukin 1 Receptor Accessory Protein (IL1RAP) in early stem or progenitor cells of the subject, wherein a subject with a high level of IL1RAP expression has a poorer likelihood of survival than a subject with a low level of IL1RAP expression, wherein a subject is defined as having a high level of IL1RAP expression if the level of IL1RAP expression in early stem or progenitor cells of the subject is equal to or greater than 1.5 (log 2 scale) the level of IL1RAP expression in early stem or progenitor cells from a control population of subjects without AML or a myelodysplastic syndrome (MDS).

Also provided are methods for predicting whether a subject with a myelodysplastic syndrome (MDS) is likely to progress to acute myeloid leukemia (AML), the method comprising testing whether $CD34^+$ stem or progenitor cells from the subject express Interleukin 1 Receptor Accessory Protein (IL1RAP) protein, wherein expression of IL1RAP protein in a greater percentage of $CD34^+$ cells in the subject compared to a control population of subjects without MDS or AML indicates that the subject with MDS is at high risk for progressing to acute myeloid leukemia (AML).

Also provided are methods for treating a subject having acute myeloid leukemia (AML) comprising administering to the subject an amount of an agent effective to inhibit expression or activity of Interleukin 1 Receptor Accessory Protein (IL1RAP) in early stem or progenitor cells.

Also provided are methods for identifying an agent for treating acute myeloid leukemia (AML), the method comprising determining whether or not the agent inhibits expression or activity of Interleukin 1 Receptor Accessory Protein (IL1RAP) in early stem or progenitor cells, wherein an agent that inhibits expression or activity of Interleukin 1 Receptor Accessory Protein (IL1RAP) in early stem or progenitor cells is identified as a candidate agent for treating acute myeloid leukemia (AML), and wherein an agent that does not inhibit expression or activity of Interleukin 1 Receptor Accessory Protein (IL1RAP) in early stem or progenitor cells is not identified as a candidate agent for treating acute myeloid leukemia (AML).

Also provided are methods for treating a subject having acute myeloid leukemia (AML) or a high risk myelodysplastic syndrome (MDS) comprising administering to the subject an agent that binds to Interleukin 1 Receptor Accessory Protein (IL1RAP) protein expressed on the surface of AML cells in a subject with AML or on the surface of early stem or progenitor cells in a subject with high risk MDS, wherein the agent is an antibody or aptamer that illicits an immune response or wherein the agent is an aptamer or antibody conjugated to a cytotoxic agent.

Also provided are methods for treating a subject having acute myeloid leukemia (AML) or a high risk myelodysplastic syndrome (MDS) comprising administering to the subject an agent that binds to ankyrin repeat domain 36B (ANKRD36B), CD97 molecule (CD97), SH2 domain protein 1A (SH2D1A) or solute carrier family 38, member 1 (SLC38A1) expressed on the surface of AML cells in a subject with AML or on the surface of early stem or progenitor cells in a subject with high risk MDS, or that binds to chemokine (C—X—C motif) ligand 2 (CXCL2) or interleukin 8 (IL8) secreted though the cell surface, wherein the agent is an antibody or aptamer that illicits an immune response or wherein the agent is an aptamer or antibody conjugated to a cytotoxic agent.

Also provided are methods for diagnosing a subject as having acute myeloid leukemia (AML) comprising testing early stem or progenitor cells from the subject for expression of two or more of the following genes: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), UPF2 regulator of nonsense transcripts homolog, aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, and C/D box 36B (SNORD36B); wherein the subject is diagnosed as having acute myeloid leukemia (AML) when expression of two or more of the tested genes is changed compared to the level of expression in a control population without AML or a myelodysplastic syndrome (MDS); wherein the following genes are overexpressed in a subject with AML compared to the level of expression in the control population: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), and UPF2 regulator of nonsense transcripts homolog; and wherein the following genes are underexpressed in a subject with AML compared to the level of expression in the control population: aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, and C/D box 36B (SNORD36B).

Also provided are methods for treating a subject having acute myeloid leukemia (AML) comprising administering to the subject an amount of one or more agents effective to i) inhibit expression or activity of one or more of the following in early stem or progenitor cells: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), or UPF2 regulator of nonsense transcripts homolog; and/or ii) increase expression or activity of one or more of the following in early stem or progenitor cells: aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, or C/D box 36B (SNORD36B).

IL1RAP mRNA expression in CD34+ cells of different types of MDS (N=183 total) with refractory anemia (RA), refractory anemia with ringed sideroblasts (RARS) and refractory anemia with excess blast types 1 (RAEB1) and 2 (RAEB2), and CD34+ cells of healthy controls (N=17). Statistical significance is indicated by asterisks (***p<0.001).

Figure 17:
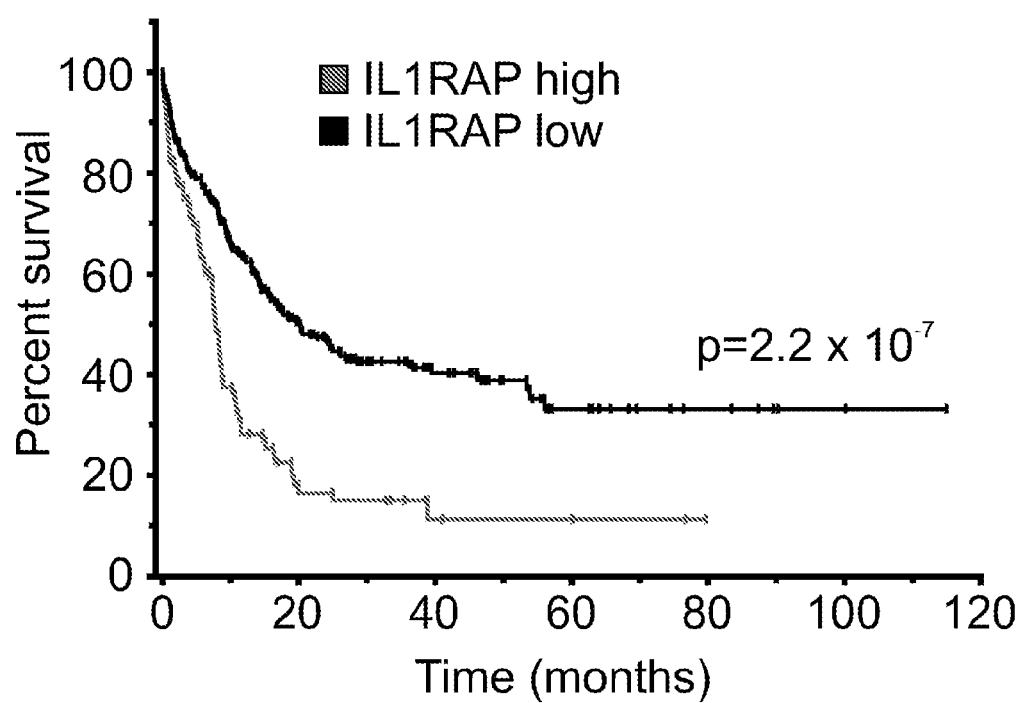

FIG. 17. IL1RAP overexpression is associated with poor clinical outcome in AML with normal karyotype. Combined survival analysis of three cohorts of AML patients with normal karyotype (n=317) dichotomized for IL1RAP gene expression levels at the 75th percentile. Overall survival of patients with low and high IL1RAP expression is shown in black and grey, respectively. Statistical significance is indicated.

Figures 18A, 18B:
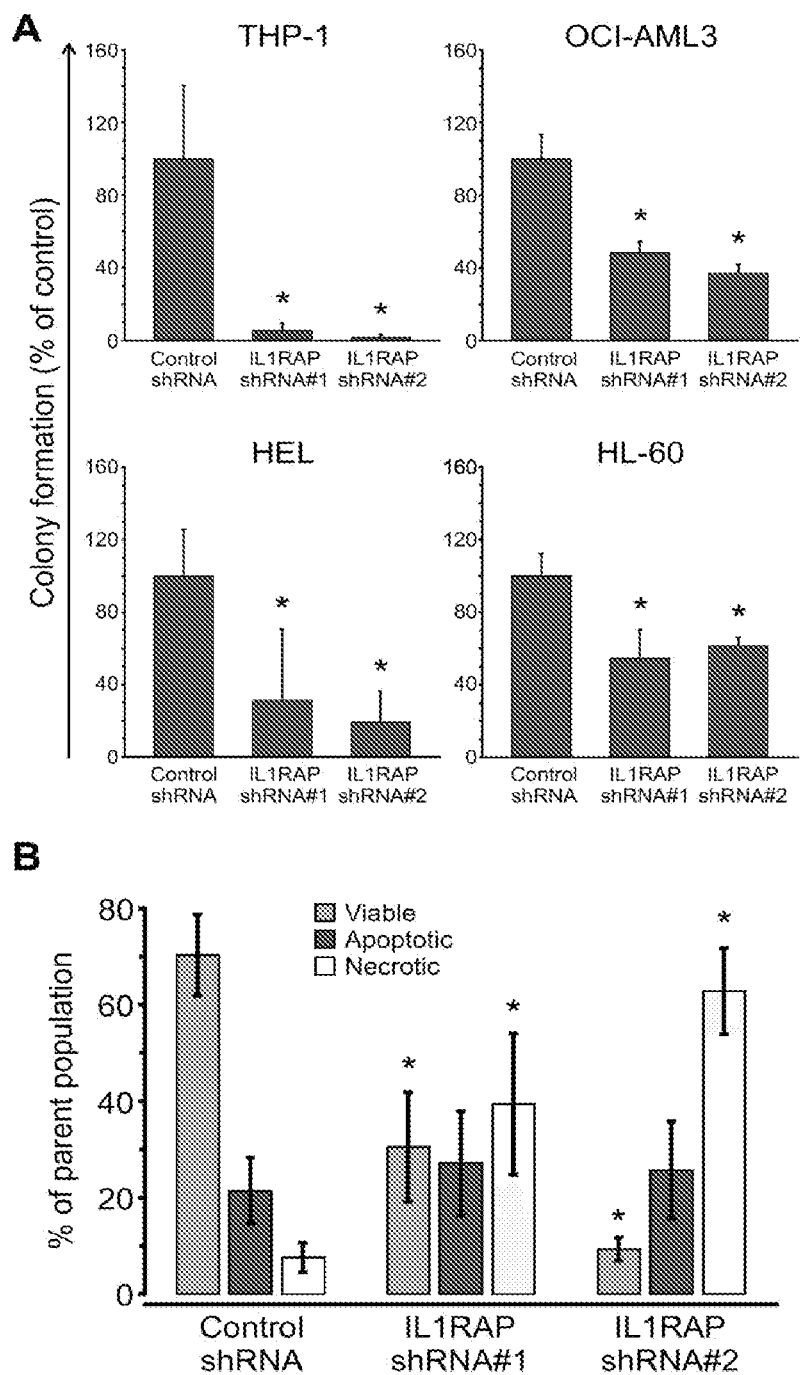

FIG. 18A-18B. IL1RAP knockdown decreases clonogenic potential and leads to increased cell death of AML cells. A) Colony formation assay in semisolid methylcellulose media of AML cells (THP-1, OCI-AML3, HEL, HL-60) infected with control and two IL1RAP-directed shRNAs. Mean and standard deviations are shown. Asterisks indicate statistical significance (p<0.05). B) Analysis of apoptosis/necrosis with Annexin V/DAPI in THP-1 cells infected with control and IL1RAP shRNAs. The plot shows mean and standard deviation of 3 independent experiments. Statistical significance is indicated (* indicate p<0.05).

Figure 19:
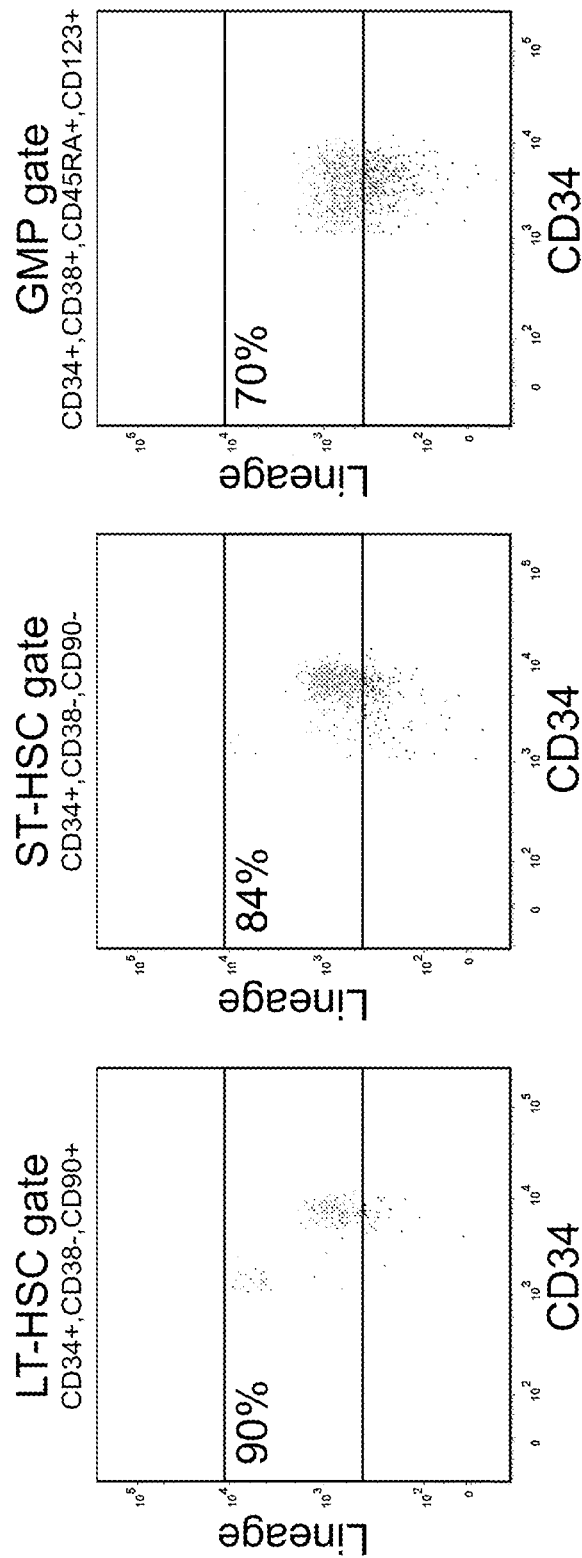

FIG. 19. Lineage exclusion is critical for stem and progenitor sorting. Analysis of lineage positive cells in phenotypic stem (LT-HSC and ST-HSC) and granulocyte-macrophage progenitor (GMP) compartments from bone marrow of a healthy donor. Percentages indicate the percentage of lineage+ cells in each compartment. Surface markers are indicated.

Figure 20:
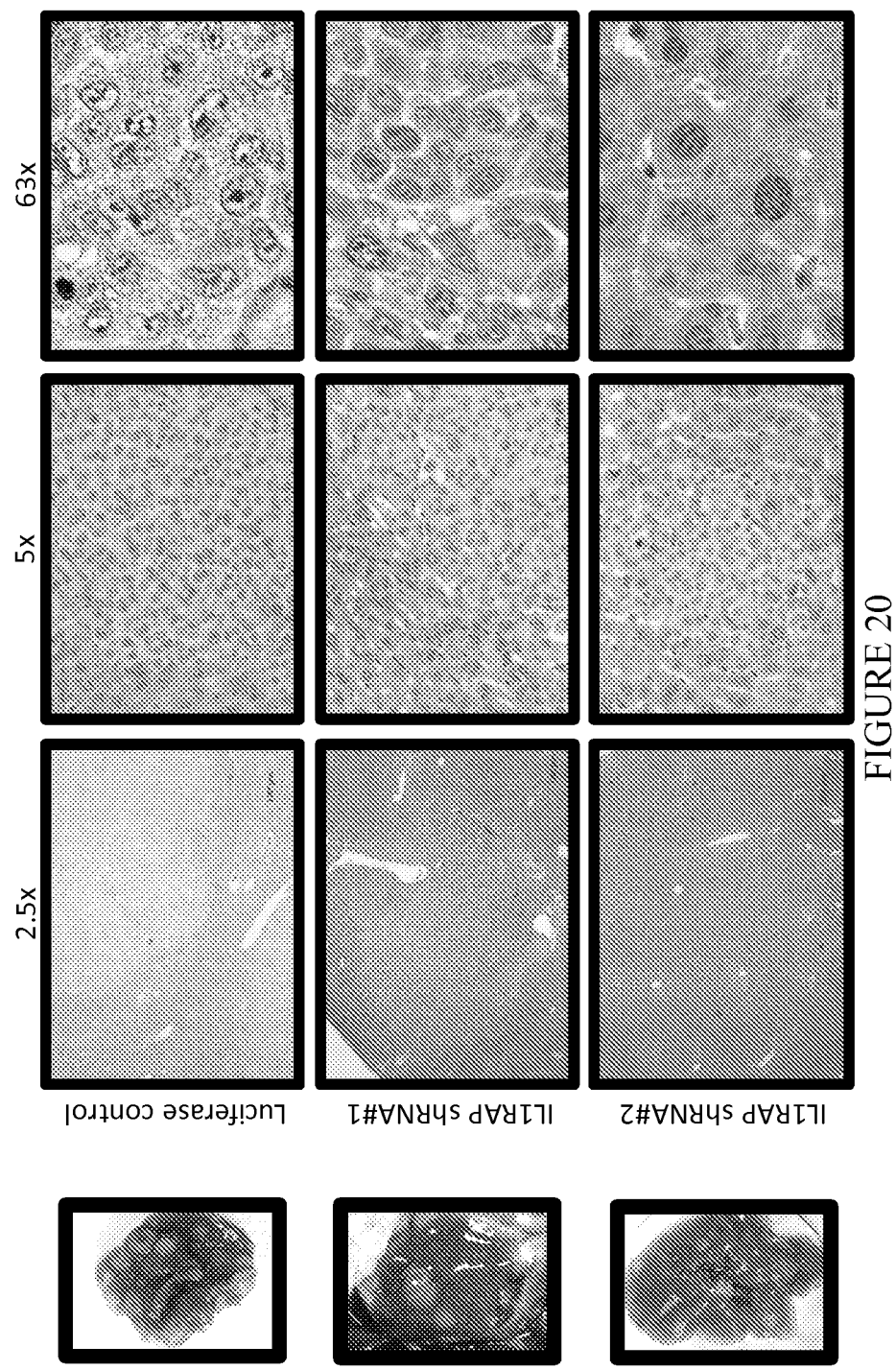

FIG. 20. Proliferation and infiltration of the liver by human AML cells is significantly inhibited by knockdown of IL1RAP. Macroscopic morphology (right) and microscopic images (left) at different magnifications of an exemplary liver of recipient mice is shown. The upper row show control treated AML cells, the lower rows show AML cells treated with 2 different shRNAs directed against IL1RAP.

Figure 21:
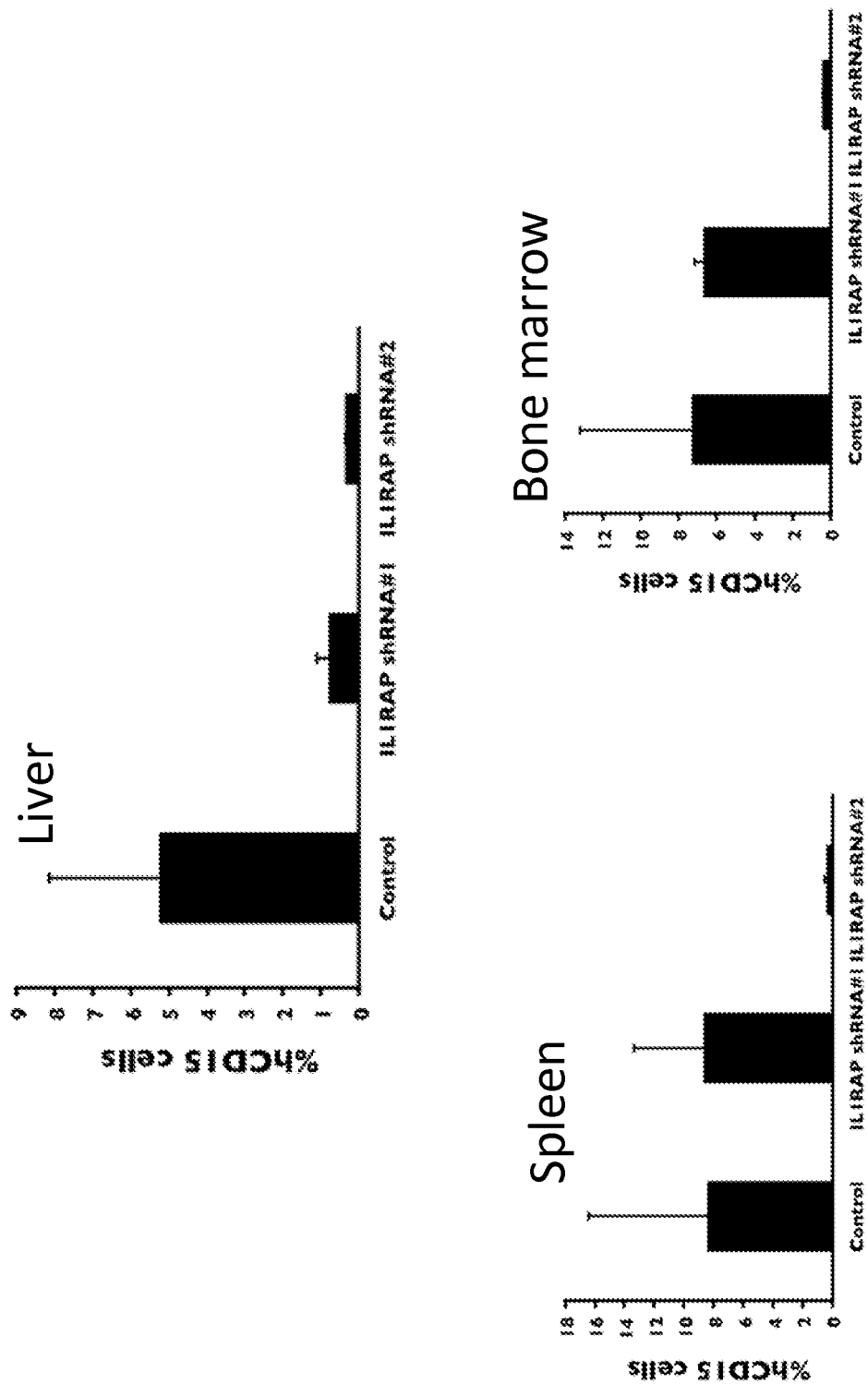

FIG. 21. Confirmation of decreased proliferation and infiltration of different hematopoietic organs through human AML cells by flow cytometry. Liver, spleen, and bone marrow are shown. Shown are control treated AML cells and AML cells treated with 2 different shRNAs directed against IL1RAP.

DETAILED DESCRIPTION OF THE INVENTION

The present invention provides a method for determining the prognosis of a subject having acute myeloid leukemia (AML) comprising determining the level of expression of Interleukin 1 Receptor Accessory Protein (IL1RAP) in early stem or progenitor cells of the subject, wherein a subject with a high level of IL1RAP expression has a poorer likelihood of survival than a subject with a low level of IL1RAP expression, wherein a subject is defined as having a high level of IL1RAP expression if the level of IL1RAP expression in early stem or progenitor cells of the subject is equal to or greater than 1.5 (log 2 scale) the level of IL1RAP expression in early stem or progenitor cells from a control population of subjects of similar age without AML or a myelodysplastic syndrome (MDS).

The present invention also provides a method for determining the prognosis of a subject having acute myeloid leukemia (AML) comprising determining the kinetics of the frequency of Interleukin 1 Receptor Accessory Protein (IL1RAP)-positive cells within early stem or progenitor cells of the subject, wherein a subject with an increase of IL1RAP-positive stem cells (>2-fold) has a higher likelihood of disease progression. This can be achieved through a method of serial determination of IL1RAP+ stem cells (Lin−CD34+) before and after different therapies and throughout the course of disease, and comparison to previously determined "baseline" percentage of IL1RAP+ stem cells.

Early stem or progenitor cells include long-term hematopoietic stem cells (LT-HSC), short-term hematopoietic stem cells (ST-HSC), and granulocyte-monocyte progenitor cells (GMP). The strategy disclosed herein includes stringent lineage depletion (exclusion of lineage antigens: CD2, CD3, CD4, CD7, CD8, CD10, CD11B, CD14, CD15, CD19, CD20, CD56, Glycophorin A) and defines the earliest stem and progenitors as follows: Lin−/CD34+/CD38−/CD90+(LT-HSC), Lin−/CD34+/CD38−/CD90− (ST-HSC), and Lin−/CD34+/CD38+/CD123+/CD45RA+ (GMP) (see also FIG. 19 on the additional stringency of the lineage exclusion).

The method can be carried out by determining the level of expression of IL1RAP mRNA or by determining the level of expression of IL1RAP protein. IL-1RAP mRNA expression can be determined, for example, by quantitative real-time PCR using the primers: FWD primer 5'-TGCATCTTTGAC-CGAGACAG-3' (SEQ ID NO:1) and REV primer CGGCT-GAAAATGCAGAAAA-3') (SEQ ID NO:2). Interleukin 1 Receptor Accessory Protein (IL1RAP) is a cell surface protein. Decection of the protein could be carried out, for example, using whole early stem or progenitor cells, membranes or fragments of membranes from the cells, or cell homogenates.

As used herein, "prognosis" covers overall and event-free survival, which also includes primary resistance to therapy, and the likelihood of relapse—features in AML that are specifically thought to arise from immature stem cell compartments. Knowledge of a subject's prognosis can be used to affect the treatment decision. For example, the prognosis may indicate that a change of (maintenance) therapy is required. Thus, the methods may further include a recommendation that the subject's therapy be, for example, changed or maintained.

Also provided is a method for predicting whether a subject with a myelodysplastic syndrome (MDS) is likely to progress to acute myeloid leukemia (AML), the method comprising testing whether Lin−CD34+ stem or progenitor cells from the subject express Interleukin 1 Receptor Accessory Protein (IL1RAP) protein, wherein expression of IL1RAP protein in a greater percentage of Lin−CD34+ cells (or a subpopulation of them) in the subject compared to a control population of subjects of similar age without MDS or AML indicates that the subject with MDS is at high risk for progressing to acute myeloid leukemia (AML).

Also provided is a method for predicting whether a subject with a myelodysplastic syndrome (MDS) is likely to progress to acute myeloid leukemia (AML), the method comprising serial testing (e.g., in a time course over the course of the disease and/or upon treatments) whether Lin−CD34+ stem or progenitor cells from the subject express Interleukin 1 Receptor Accessory Protein (IL1RAP) protein, wherein expression of IL1RAP protein in a greater (e.g., more than 2-fold) percentage of Lin−CD34+ cells (or a subpopulation of them) in the subject compared to a percentage determined at an earlier time point indicates that the subject with MDS is at high risk for progressing to acute myeloid leukemia (AML).

Myelodysplastic syndromes (MDS) involve ineffective production or abnormal development of myeloid blood cells, and include refractory anemia (RA) or refractory cytopenia with unilineage dysplasia, refractory anemia with ringed sideroblasts (RARS), refractory cytopenia with multilineage dysplasia (RCMD), refractory anemia with excess blasts (RAEB), refractory anemia with excess blasts in transformation (RAEB-T), chronic myelomonocytic leukemia (CMML) (not to be confused with chronic myelogenous leukemia or CML), and 5q− syndrome.

Expression of IL1RAP protein in at least 10% of Lin$^-$CD34$^+$ cells from the subject with MDS indicates that the subject is at high risk for progressing to acute myeloid leukemia (AML). Subjects at high risk for progressing to AML include subjects with refractory anemia with excess blasts (RAEB).

Expression of IL1RAP protein in less than 2% of Lin$^-$CD34$^+$ cells indicates that the subject with MDS is at low risk for progressing to acute myeloid leukemia (AML). Subjects at low risk for progressing to AML include subjects with refractory cytopenia with multilineage dysplasia (RCMD).

CD34 is a cell surface glycoprotein that can be readily detected using available antibodies. CD34$^+$ cells are cells that express CD34 on their cell surface. CD38 is another cell surface glycoprotein, which can also be detected using available antibodies. In one embodiment, the CD34$^+$ stem and progenitor cells do not express CD38 (i.e., CD34$^+$/CD38$^-$ cells). Other lineage surface markers are mentioned and explained herein above.

Also provided is a method for treating a subject having acute myeloid leukemia (AML) comprising administering to the subject an amount of an agent effective to inhibit expression or activity of Interleukin 1 Receptor Accessory Protein (IL1RAP) in early stem or progenitor cells. Preferably, treatment with the agent inhibits division of AML cells. AML cells are defined as any cell type that is part of the malignant clone.

Importantly, as show herein for the first time, inhibition of IL1RAP is functionally effective in AML cells, and thus targeting/inhibiting IL1RAP itself is a viable therapeutic strategy in AML/MDS. Previous studies and patents had only shown that IL1RAP can be used as a surface label/marker to direct cytotoxic T cells to malignant cells, which then leads to their killing (15, 16).

The agent may be, for example, a small molecule, an antibody or antibody fragment, an aptamer or a molecule such as RNA that inhibits gene expression through RNA interference, such as a small hairpin RNA or short hairpin RNA (shRNA). Antibody fragments include, but are not limited to, F(ab')$_2$ and Fab' fragments and single chain antibodies. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies. The antibody can be a human antibody or a non-human antibody such as a goat antibody or a mouse antibody. Antibodies can be "humanized" using standard recombinant DNA techniques.

Also provided is a method for identifying an agent for treating acute myeloid leukemia (AML), the method comprising determining whether or not the agent inhibits expression or activity of Interleukin 1 Receptor Accessory Protein (IL1RAP) in early stem or progenitor cells (Lin−CD34+ or subfraction thereof), wherein an agent that inhibits expression or activity of Interleukin 1 Receptor Accessory Protein (IL1RAP) in early stem or progenitor cells is identified as a candidate agent for treating acute myeloid leukemia (AML), and wherein an agent that does not inhibit expression or activity of Interleukin 1 Receptor Accessory Protein (IL1RAP) in early stem or progenitor cells is not identified as a candidate agent for treating acute myeloid leukemia (AML).

Preferably, the agent treats AML by inhibiting division of AML cells.

The method can be carried out by determining the level of expression of IL1RAP mRNA or by determining the amount or activity of IL1RAP protein.

The method can be carried out by determining the kinetics of the percentage of cells within the total Lin$^-$CD34$^+$ population (or subfraction thereof) expressing IL1RAP protein, before and after treatment with an agent.

Also provided is a method for treating a subject having acute myeloid leukemia (AML) or a high risk myelodysplastic syndrome (MDS) comprising administering to the subject an agent that binds to Interleukin 1 Receptor Accessory Protein (IL1RAP) protein expressed on the surface of AML cells in a subject with AML or on the surface of early stem or progenitor cells in a subject with high risk MDS, wherein the agent is an antibody or aptamer that illicits an immune response or wherein the agent is an aptamer or antibody conjugated to a cytotoxic agent.

Also provided is a method for treating a subject having acute myeloid leukemia (AML) or a high risk myelodysplastic syndrome (MDS) comprising administering to the subject dendritic cells that have been engineered to present Interleukin 1 Receptor Accessory Protein (IL1RAP) protein or immunogenic parts of IL1RAP protein on their surface. Such dendritic cells can be given to subjects with AML or MDS who express IL1RAP protein on the surface of early stem or progenitor cells.

Also provided is a method for treating a subject having acute myeloid leukemia (AML) or a high risk myelodysplastic syndrome (MDS) comprising administering to the subject one or more agents that binds to ankyrin repeat domain 36B (ANKRD36B), CD97 molecule (CD97), SH2 domain protein 1A (SH2D1A) or solute carrier family 38, member 1 (SLC38A1) expressed on the surface of AML cells in a subject with AML or on the surface of early stem or progenitor cells in a subject with high risk MDS, or that binds to chemokine (C—X—C motif) ligand 2 (CXCL2) or interleukin 8 (IL8) secreted though the cell surface, wherein the agent is an antibody or aptamer that illicits an immune response or wherein the agent is an aptamer or antibody conjugated to a cytotoxic agent. CD97, ANKRD36B, SH2D1A and SLC38A1 are membrane proteins. CXCL2 and IL8 are cytokines that are secreted through the membrane, which means they are at least transiently at the cell surface. CXCL2 and IL8 likely play a role in paracrine stimulation, which means they may also be good targets once they are bound to their target cells.

Examples of cytotoxic agents include radioisotopes and chemotherapeutic agents.

To treat a subject with a myelodysplastic syndrome (MDS) or with acute myeloid leukemia (AML) means to reduce a sign or symptom of the disease or to reduce or halt progression of the disease. AML is characterized by the rapid growth of abnormal white blood cells that accumulate in the bone marrow and interfere with production of normal blood cells. Signs and symptoms of AML include a drop in red blood cells (anemia), which can cause can cause fatigue, paleness, and shortness of breath, a drop in platelets, which can lead to bruising and bleeding, and a drop in normal white blood cells, which makes the patient susceptible to infection. AML progresses rapidly and is typically fatal within weeks or months if left untreated. Signs and symptoms of MDS also include anemia, low neutrophil count leading to increased susceptibility to infection, and low platelet count causing to increased susceptibility to bruising and bleeding. Subjects with MDS who progress to AML usually do so within months to a few years.

Therapeutic agents can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intranasal administration, and administration through an osmotic minipump. The compounds can be applied to the skin, for example, in compositions formulated as skin creams, or as sustained release formulations or patches.

Also provided is a method for diagnosing a subject as having acute myeloid leukemia (AML) comprising testing early stem or progenitor cells from the subject for expression of two or more of the following genes: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), UPF2 regulator of nonsense transcripts homolog, aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, and C/D box 36B (SNORD36B);

wherein the subject is diagnosed as having acute myeloid leukemia (AML) when expression of two or more of the tested genes is changed compared to the level of expression in a control population of similar age without AML or a myelodysplastic syndrome (MDS);

wherein the following genes are overexpressed in a subject with AML compared to the level of expression in the control population: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), and UPF2 regulator of nonsense transcripts homolog; and wherein the following genes are underexpressed in a subject with AML compared to the level of expression in the control population: aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, and C/D box 36B (SNORD36B).

Preferably, the method comprises testing early stem or progenitor cells from the subject for expression of two or more of the following genes: ankyrin repeat domain 36B (ANKRD36B), interleukin 8 (IL8), interleukin 1 receptor accessory protein (IL1RAP), leucine rich repeat (in FLII) interacting protein 1 (LRRFIP1), microRNA21 (mir-21), RAS guanyl releasing protein 3 (RASGRP3), spermidine/spermine N1-acetyltransferase 1 (SAT1), brain expressed, X-linked 5 (BEX5), insulin-like growth factor 1 receptor (IGF1R), LOC401097, and nuclear factor I/A (NFIA);

wherein the subject is diagnosed as having acute myeloid leukemia (AML) when expression of two or more of the tested genes is changed compared to the level of expression in a control population without AML or a myelodysplastic syndrome (MDS);

wherein the following genes are overexpressed in a subject with AML compared to the level of expression in the control population: ankyrin repeat domain 36B (ANKRD36B), interleukin 8 (IL8), interleukin 1 receptor accessory protein (IL1RAP), leucine rich repeat (in FLII) interacting protein 1 (LRRFIP1), microRNA21 (mir-21), RAS guanyl releasing protein 3 (RASGRP3), and spermidine/spermine N1-acetyltransferase 1 (SAT1); and wherein the following genes are underexpressed in a subject with AML compared to the level of expression in the control population: brain expressed, X-linked 5 (BEX5), insulin-like growth factor 1 receptor (IGF1R), LOC401097, and nuclear factor I/A (NFIA).

These genes occur at the common intersection shown in the Venn diagrams in FIGS. 8-14, and as listed in Tables I.2, II.2, III.2, A.1, B.1 and C.1.

The level of expression can be tested at the RNA level or at the protein level. The method can be carried out using, for example, a microarray of oligonucleotide probes, multiplex polymerase chain reaction (PCR), massively parallel sequencing, and antibody array, or mass spectrometry.

In one embodiment, the subject is diagnosed as having acute myeloid leukemia (AML) when expression of all of the tested genes is changed compared to the level of expression in a control population of similar age without AML or a myelodysplastic syndrome (MDS).

Preferably, subjects are matched to controls of similar age. For example, subjects and controls can be matched within an age range of, e.g., 55-60 years or 60-65 years.

Also provided is a method for treating a subject having acute myeloid leukemia (AML) comprising administering to the subject an amount of one or more agents effective to i) inhibit expression or activity of one or more of the following in early stem or progenitor cells: ankyrin repeat domain 36B (ANKRD36B), B double prime 1, subunit of RNA polymerase III transcription initiation factor IIIB (BDP1), CD97 molecule (CD97), chemokine (C—X—C motif) ligand 2 (CXCL2), coiled-coil domain containing 88A (CCDC88A), cyclin T1 (CCNT1), eukaryotic translation initiation factor 5B (EIF5B), interleukin 8 (IL8), interleukin 1 receptor accessory protein (IL1RAP), leucine rich repeat (in FLII) interacting protein 1 (LRRFIP1), microRNA21 (mir-21), nuclear factor of kappa light polypeptide gene enhancer in B-cells inhibitor, alpha (NFKBIA), protein phosphatase 1, regulatory subunit 15A (PPP1R15A), 6-pyruvoyltetrahydropterin synthase (PTS), RAS guanyl releasing protein 3 (RASGRP3), SH2 domain protein 1A (SH2D1A), solute carrier family 38, member 1 (SLC38A1), spermidine/spermine N1-acetyltransferase 1 (SAT1), or UPF2 regulator of nonsense transcripts homolog; and/or ii) increase expression or activity of one or more of the following in early stem or progenitor cells: aldehyde dehydrogenase 1 family, member A1 (ALDH1A1), brain expressed, X-linked 5 (BEX5), carbonic anhydrase I (CA1), desmoglein 2 (DSG2), deoxynucleotidyltransferase, terminal (DNTT), hemoglobin, beta (HBB), immunoglobulin J polypeptide (IGJ), insulin-like growth factor 1 receptor (IGF1R), LOC401097, nuclear factor I/A (NFIA), nudix (nucleoside diphosphate linked moiety X)-type motif 11 (NUDT11), procollagen-lysine, 2-oxoglutarate 5-dioxygenase 2 (PLOD2), ribosomal protein L39-like (RPL39L), serpin peptidase inhibitor, clade E, member 2 (SERPINE2), small nucleolar RNA, H/ACA box 42 (SNORA42), small nucleolar RNA, C/D box 46 (SNORD46), small nucleolar RNA, or C/D box 36B (SNORD36B).

Preferably, the method comprises administering to the subject an amount of one or more agents effective to i) inhibit expression or activity of one or more of the following in early stem or progenitor cells: ankyrin repeat domain 36B (ANKRD36B), interleukin 8 (IL8), interleukin 1 receptor accessory protein (IL1RAP), leucine rich repeat (in FLII) interacting protein 1 (LRRFIP1), microRNA21 (mir-21), RAS guanyl releasing protein 3 (RASGRP3), or spermidine/spermine N1-acetyltransferase 1 (SAT1); and/or ii) increase expression or activity of one or more of the following in early stem or progenitor cells: brain expressed, X-linked 5 (BEX5), insulin-like growth factor 1 receptor (IGF1R), LOC401097, or nuclear factor I/A (NFIA).

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

A transcriptional analysis was undertaken in parallel of multiple precisely defined and highly purified stem and progenitor populations in acute myeloid leukemia, in order to avoid the heterogeneous bulk population. To further reduce heterogeneity and experimental noise, the initial focus was on one particular, genetically defined subset of AML, AML with monosomy 7 as the sole cytogenetic aberration, for transcriptional analysis and candidate target identification. The study was then extended to other AML subtypes and MDS. Specifically, sorted cell populations from patients with AML with complex karyotype, and AML with normal karyotype were included in the analysis, and genes within these novel data sets were cross-compared. The unique strength of this novel approach is 2-fold. First, it allows for the first time the identification of novel candidate genes that are consistently deregulated at multiple immature stem and progenitor cell stages, and thus targeting them may be efficient at all relevant pre-leukemic cell stages including leukemia-cells-of origin. Second, the cross-comparison and intersection of deregulated transcription in stem cells across various well-defined subtypes of leukemia reveals common aberrant gene expression, which is likely to be functionally critical in stem cells of AML patients independent of the specific disease subtypes. Thus, these targets are expected to be particularly promising therapeutic targets.

The present studies employed a novel strategy of parallel transcriptional analysis of multiple phenotypic stem and progenitor populations from individuals with AML, including long-term HSC (the earliest definable stem cell population; represents only about 1% of cells within the total CD34+ population, and less than 10% within CD34+CD38- cells), short-term HSC, and granulocyte-monocyte progenitors (GMP), and comparison to corresponding cell populations from age-matched healthy controls (HC). Importantly, in contrast to previously used strategies, the present cell sorting method includes a stringent exclusion of "lineage markers" (Lin−), which have recently been demonstrated to be clearly superior in terms of the reached stringency and purity of stem cell populations (2); see also FIG. 19 for a direct comparison of sorting with and without lineage exclusion gate), in comparison to previously applied strategies (15).

Methods

Patient Samples and Cell Lines.

Bone marrow (BM) samples from thirty five patients with AML, and from six patients with MDS were obtained within the framework of routine diagnostic bone marrow aspirations after written informed consent. All experiments were approved by the institutional review board of the Albert Einstein College of Medicine (CCI#2008-942). Healthy Bone Marrow specimens were purchased from Stem Cell Technologies Inc. HL-60, OCI-AML3, HEL, MOLM-13 and THP-1 cell lines were growth in 90% RPMI medium supplemented with 10% Fetal Bovine Serum (FBS) and antibiotics. UT-7 cell line was maintained in alpha-MEM medium supplemented with 20% FBS, 5 ng/microliter of GM-CSF and antibiotics.

Multi-Parameter High Speed FACS-Sorting of Stem and Progenitor Cells.

To purify the stem and progenitor compartments from total BM from AML or MDS, samples were processed as follows: frozen BM aspirates were quickly thawed in a water bath at 37° C., and resuspended in Iscove's modified Dulbecco's medium supplemented with 2% FBS. After repeated washes, cells were resuspended in MACS buffer (Phosphate Buffer Saline (PBS) supplemented with 0.5% Bovine serum albumin (BSA) and 2 mM EDTA, pH 7.2). CD34$^+$ cells were immunomagnetically selected from mononuclear cells from AML and healthy patients utilizing Miltenyi Macs technology (130-046-702, MiltenyiBiotech) following manufacture's protocol. Afterwards, cells were stained for 30 minutes on ice with PE-Cy5 conjugated antibodies against lineage-antigens (CD2[RPA-2.10], CD3[UCHT1], CD4 [S3.5], CD7[6B7], CD8[3B5], CD10[CB-CALLA], CD11b [VIM12], CD14[TueK4], CD19[HIB19], CD20[2H7], CD56[MEM-188], Glycophorin A [CLB-ery-1(AME-1)]), and hematopoietic stem and progenitor markers (APC conjugated CD34[581/CD34(class III epitope), PE-CY7 conjugated CD38[HIT-2], FITC conjugated CD45RA[MEM-56], PE conjugated CD123[6H6] and APC-Cy7 conjugated CD90[5E10]) in order to distinguish LT-HSC (Lin$^-$/CD34$^+$/CD38$^-$/CD90$^+$), ST-HSC (Lin$^-$/CD34$^+$/CD38$^-$/CD90$^-$) and GMP (Lin$^-$/CD34$^+$/CD38$^+$/CD123$^+$/CD45RA$^+$). After staining, cells were washed with MACS buffer and subjected to 7-color 5 waysorting utilizing a FACSAria II Special Order System (BD Biosciences, San Jose, Calif.) as previously described (9). Cells were sorted directly in RLT plus buffer (Qiagen, La Jolla Calif.) for RNA extraction.

RNA Amplification and Genome-Wide Transcriptional Analysis.

Total RNA was extracted from sorted LT-HSC, ST-HSC and GMP populations from AML and healthy controls using a denaturing buffer containing guanidine isothiocyanate (ALLPrep Micro Kit, Qiagen). After checking the quality of RNA with an Agilent2100 Bioanalyzer, total RNA was amplified utilizing Single Primer Isothermal Amplification (SPIA® Nugen Ovation pico WTA) system according to the manufacturer's instructions. After labeling with the GeneChip® WT terminal labeling kit (Affymetrix), labeled cRNA of each individual sample was hybridized to GeneChip® Human Gene 1.0 ST microarray (Affymetrix), stained, and scanned by GeneChip® Scanner 3000 7G system (Affymetrix) according to standard protocols. Array data was normalized in Expression Console™ software from Affymetrix using Robust Multichip Algorithm. Normalized data were analyzed in CLC Genomic Workbench software v4.5.1 (CLC Bio, Aarhus, Denmark) for differential gene expression between groups using Student's t test with a significance level of P<0.05. Genes with an absolute value of the group mean difference equal or greater than 1.5 (log 2 scale) and p-values smaller than 0.05 were considered to be differentially expressed between groups.

Validation of IL1RAP Overexpression.

IL-1RAP mRNA expression was corroborated in AML patient samples and healthy controls by quantitative real-time PCR (FWD primer 5'-TGCATCTTTGACCGA-GACAG-3' (SEQ ID NO:1), REV primer CGGCT-GAAAATGCAGAAAA-3') (SEQ ID NO:2) using complementary DNA amplified from total RNA with the WT-Ovation RNA Amplification System (Nugen) with SYBR® Green on an iQ5real-time PCR instrument (Bio-Rad). Abundance of each transcript was calculated using the Pfaffl Method. IL-1 RAP expression was validated at the protein level by Flow cytometry using a FACSAria II Special Order System (BD Biosciences, San Jose, Calif.) using abiotinylated IL-1RAP antibody (R&D Systems, Cat#BAF676) and Streptavidin APC-Alexa Fluor® 750 conjugate (SA1027, Invitrogen) as a secondary antibody. For flow cytometry, AML and healthy control patient samples were processed as described in the "Multi-parameter high speed FACS-sorting of stem and progenitor cells" section with the addition of IL1RAP antibody at a final concentration of 25 microgram/milliliter. Biotinylated normal goat IgG antibody (BAF108, R&D systems) was used as an isotype control.

Fluorescence In Situ Hybridization (FISH).

Il-1rap positive and negative populations were sorted in MACS buffer and spinned onto polylysine coated slides in a StatSpin® Cytofuge 2 at minimum speed for 6 minutes. Slides were fixed with Carnoy's solution and stained with FISH probes according to standard procedures.

Lentiviral Vectors and Transduction.

For knockdown studies, shRNA template oligonucleotides (Luciferase Control shRNA: 5'-gtgcgttgttagtactaatc-ctattt-3' (SEQ ID NO:3); IL-1RAP shRNA 1: 5'-tggccttactct-gatctggtattggacta-3' (SEQ ID NO:4); IL-1RAP shRNA 2: 5'-cgggcattaattgatttcctactatattc-3') (SEQ ID NO:5) were cloned into the pSIH1-H1-copGFP shRNA vector system (System Biosciences, Mountain View, Calif.). For production of lentiviral particles, lentiviral constructs with packaging vectors were transfected into 293T producer cells using Fugene HD transfection reagent (Roche). Supernatant was harvested after 48 and 72 hours, and concentrated by ultracentrifugation. For knockdown studies, HL60, HEL, OCI-AML3, MOLM-13, THP1 and UT-7 cell lines were transfected with the short-hairpin-containing lentivirus (MOI=10), incubated for 48 or 72 hours. After culture with fresh medium, GFP-positive cells were sorted using a FACS Aria II sorter (BD Biosciences) and used for experiments. Level of knockdown of Il-1RAP was determined by flow cytometry.

Cell Proliferation Assays.

For CellTracker™ Orange CMRA (Molecular Probes) assays, 1×10$^5$ cells per well were plated into 24-well plate with 1 ml of culture medium and incubated for 45 minutes with 5 µM dye solution under growth conditions. Cells were washed with PBS, resuspended in complete medium and incubated for 30 minutes at 37° C., 5% CO$_2$. 200 nl of culture were removed, washed with PBS and assayed by flow cytometry using a FACSAria II Special Order System (BD Biosciences, San Jose, Calif.). Cells were stained with 4',6-diamidino-2-phenylindole (DAPI) before flow cytometric analysis.

For MTS assays, 1×10$^4$ cells per well were plated into 96-well plates with 100 µL culture medium. After incubation with 20 µl of MTS reagent (CellTiter 96® AQueous One Solution Cell Proliferation Assay kit, Promega), OD490 and OD650 were detected by a microplate reader (Versa max, Molecular probe). Raw values were compensated by subtraction of background, defined as [OD490–OD650] of a well with cells minus [OD490–OD650] of a well with medium only. Manual cell counts were performed culturing 1×10$^5$ cells per well in 24-well plates with 1 ml medium. Viable cells were counted using trypan blue exclusion and re-adjusted to 1×10$^5$ cells per well every 4 days.

Flow Cytometric Determination of Apoptosis.

In order to determine viability after Il-1RAP knockdown, 1×10$^6$ cells were washed with PBS and mixed with pre-diluted annexin V PE conjugated (BD Pharmigen) and DAPI. Cells were stained at room temperature for 15 minutes and resuspended in 0.5 milliliters of Annexin-V-FLUOS incubation buffer (Roche) for analysis.

Cell Cycle Analysis.

Cell cycle analysis was performed as previously described. In short, 1×10$^6$ cells were rinsed with ice-cold PBS, incubated 45 minutes at 37° C. in the dark with 0.5 milliliters Hoechst buffer (20 µg/ml Hoechst 33342 in Hanks Balance saline solution (HBSS) containing 10% FBS, 20 mM HEPES pH 7.2, 1 g/l glucose and 50 µg/ml Verapamil). Pyronin was added at 1 µg/ml and cells were incubated for 15 minutes at 37° C. in the dark, washed with PBS and analyzed by flow cytometry using a FACSAria II Special Order System (BD Biosciences, San Jose, Calif.).

Survival Studies.

Publicly available gene expression data sets from human AML studies with the accession numbers GSE12417 (training set hybridized to Affymetrix U133A and U133B microarrays; test set to U133plus2.0) and GSE10358 (U133plus2.0) were analyzed. CEL files were downloaded from GEO, and processed using GenePattern (Broad Institute, Cambridge Mass.) for normalization (ExpressionFileCreator algorithm) according to the preset parameters of the software (RMA method, with quintile normalization, background correction, median scale normalization method) and collapsing (using CollapseDatast with default parameters). All aforementioned datasets were then analyzed separately to dichotomize the population of patients of each dataset into subsets with high versus low expression of IL1RAP transcript, using the 75th percentile of normalized IL1RAP expression in each data set as the cutoff point. Publicly available clinical annotation accompanying each one of these data sets was then used to perform Kaplan-Meier survival analysis (GraphPad Prism 5.0) comparing clinical outcomes of patients with high versus low IL1RAP expression. Multivariate analysis with stepwise forward and backward model selection by Aikake Information Criterion (AIC) was performed in R/Bioconductor using the survival and MASS packages. The model parameters included IL1RAP status, FAB subclass, FLT3 mutation status, age, gender, and cytogenetic risk. IL1RAP gene expression comparisons between CD34+ cells from healthy donors and patients with chromosome 7 deletions were carried out using the published GSE14468 patient data. CEL files from del(7) patients (n=18) and healthy controls (n=11) were RMA-normalized, and log 2-transformed IL1RAP expression was plotted. Gene expression data and clinical information from 183 MDS CD34+ cells and 17 controls (17) were analyzed. IL1RAP expression was represented as scatter plots using GraphPad Prism Software (Version 5.0).

Results

Identification of Genes Consistently Dysregulated in Multiple Distinct Stem and Progenitor Cell Compartments in Patients with AML.

Figure 1:
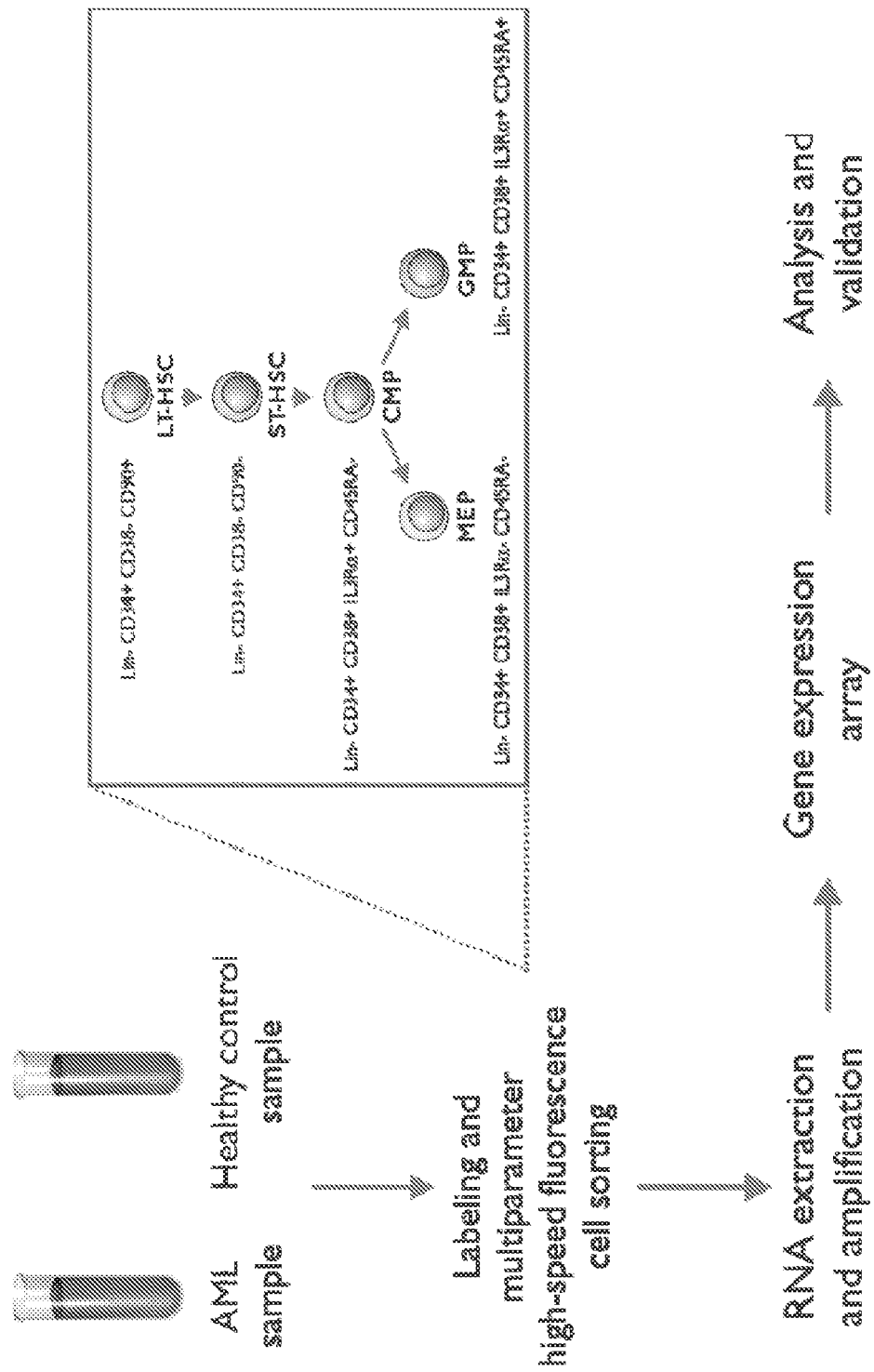
FIG. 1. Stem cell global transcriptome analysis identifies functionally relevant changes of gene expression in AML. LT-HSC: long-term hematopoietic stem cells, ST-HSC: short-term hematopoietic stem cells, CMP: common myeloid progenitors, GMP: granulocyte-monocyte progenitor, MEP: megakaryocyte-erythrocyte progenitor.
Figure 2:
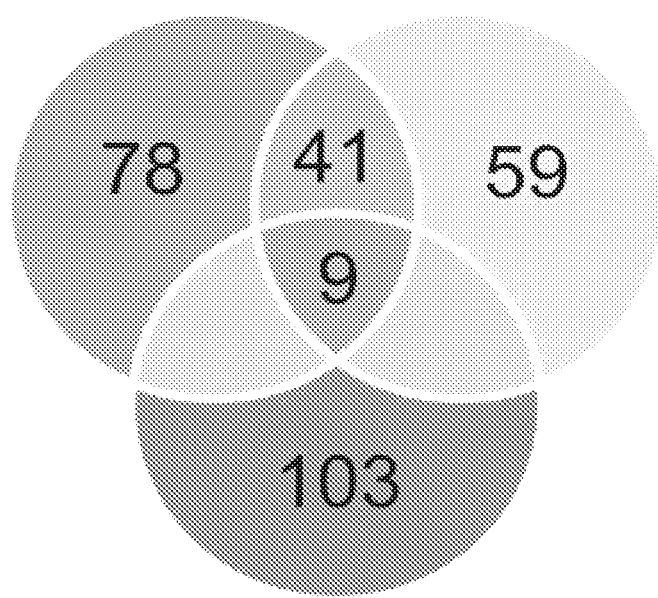
FIG. 2. Venn diagram of differential gene expression AML vs. Normal in different stem and progenitor subsets. Upper left—Δ(LT-HSC), upper right—Δ(ST-HSC), bottom—Δ(GMP).
Figure 3:
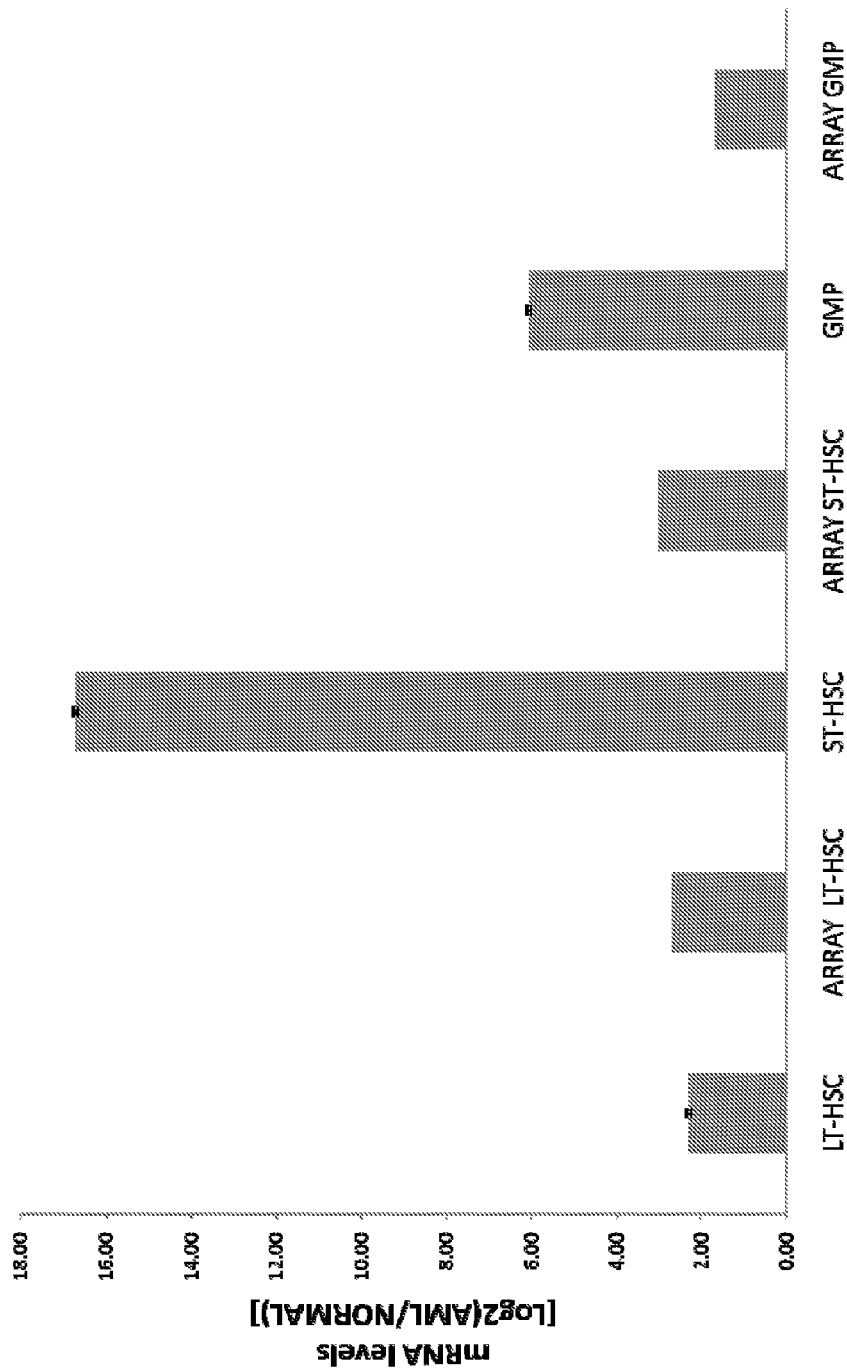
FIG. 3. Higher expression of Interleukin 1 Receptor Accessory Protein (IL1RAP) in AML stem and progenitor cells versus healthy control. qRT-PCR analysis—LT-HSC, ST-HSC, GMP; microarray analysis—ARRAY LT-HSC (n=5), ARRAY ST-HSC (n=6), ARRAY GMP (n=5).
Figure 4:
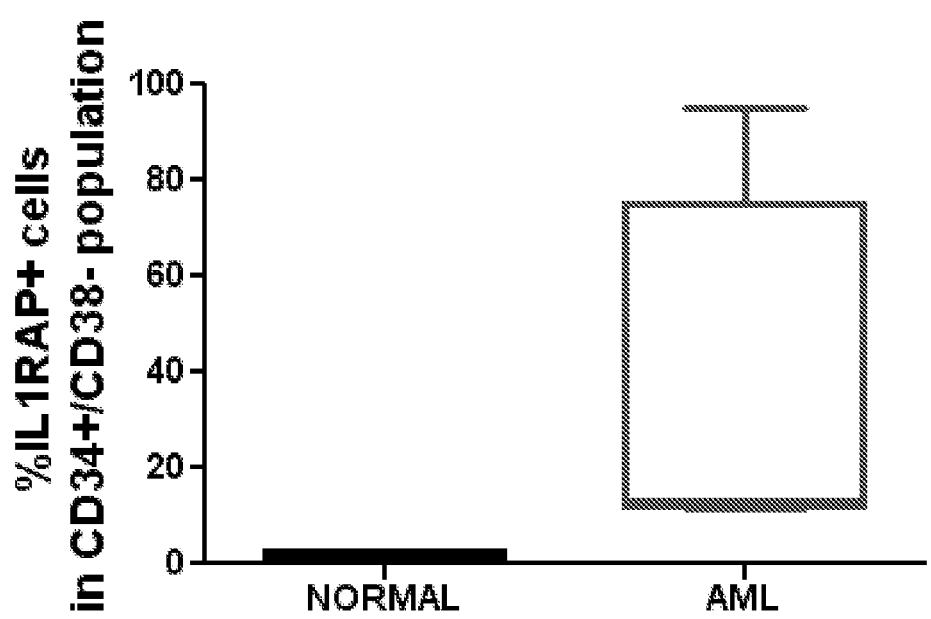
FIG. 4. A significantly larger fraction of cells within the CD34+/CD38− stem cell compartment expresses IL1RAP surface protein in AML leukemia stem cells vs. normal controls. N=8.
Figures 14A, 14B, 14C:
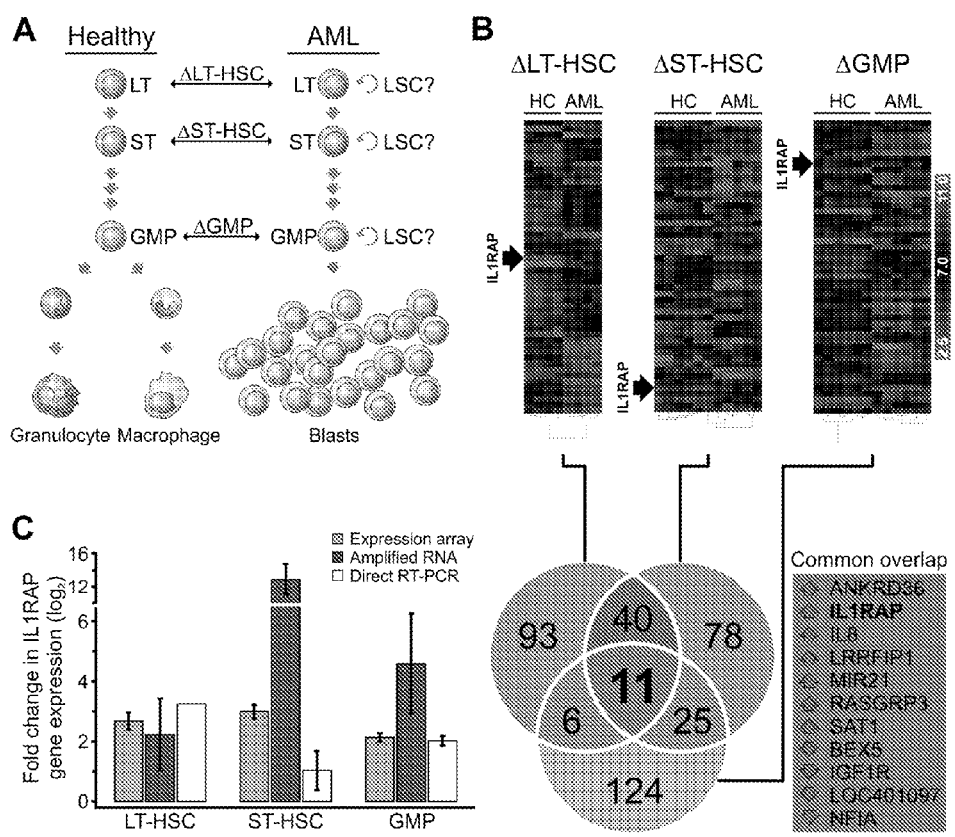
FIG. 14A-14C. A novel strategy of parallel transcriptional profiling of phenotypic hematopoietic stem and progenitor compartments of AML patients with monosomy 7 identifies overexpression of IL1RAP. A) Schematic showing the cell types used for pairwise comparison of gene expression. Phenotypically defined hematopoietic stem and progenitor compartments with potential leukemia stem cell (LSC) activity were sorted and compared between healthy and AML individuals. The symbol "Δ" refers to the gene expression differences between groups in each phenotypically defined compartment: Long-term hematopoietic stem cells (LT-HSC), short-term HSC (ST-HSC) and granulocyte-macrophage progenitors (GMP) B) Hierarchical clustering of the 50 most significantly dysregulated genes in −7 AML in phenotypically defined LT-HSC, ST-HSC and GMP of AML patients (AML) compared with healthy controls (HC). Heat maps of log 2-transformed gene expression levels are shown (top). Position of IL1RAP is indicated. Venn diagram (bottom) shows the number of differentially expressed genes that are shared between, or restricted to, specific compartments between AML samples and HC. The numbers represent the total of up- or down-regulated genes in each pairwise comparison. Genes in the triple intersection (common overlap) are listed. Up and down arrows indicate overexpression and downregulation in the AML samples, respectively. C) Validation of IL1RAP mRNA expression in LT-HSC, ST-HSC and GMP. Light grey bars show expression levels in the gene expression array (n=4 for LT-HSC, n=5 for ST-HSC and n=6 for GMP), dark grey bars show mRNA levels determined by qRT-PCR in amplified RNA (n=2), and white bars represent the mRNA levels measured by qRT-PCR from unamplified cDNA (n=1 for LT-HSC and n=2 for ST-HSC and GMP). mRNA levels were normalized to GAPDH. Fold change compared to healthy control is shown.

In this study, gene expression analysis was carried out of highly fractionated stem and progenitor cell compartments from individual patients with AML with monosomy 7 (−7) or deletions of the long arm of chromosome 7 (7q−) as the sole cytogenetic aberration, in comparison to phenotypically identical cell populations from age-matched healthy controls, in an attempt to reduce inter-patient as well as cellular heterogeneity. Specifically, Lin−CD34+CD38−CD90+ cells (referred to as LT-HSC), Lin−CD34+CD38−CD90− cells (referred to as ST-HSC), and Lin−CD34+CD38+CD123+ CD45RA+ cells (referred to as GMP) were sorted and analyzed, utilizing previously established marker schemes (Refs 7-8, 18-19). Rigorous lineage depletion was included in order to avoid analysis of the leukemic bulk (blast) population and to focus on the earliest known stem cell and committed myeloid progenitor populations in humans. Lineage depletion eliminated 70-90% of lineage marker-positive cells from the stem and progenitor compartments (FIG. 19). To identify genes dysregulated within the distinct stem and progenitor cell compartments of AML patients, Affymetrix GeneST 1.0 arrays were used to compare gene expression with the respective healthy controls (HC) at each cellular level (AML-LT-HSC versus HC-LT-HSC, AML-ST-HSC versus HC-ST-HSC, and AML-GMP versus HC-GMP (FIG. 1, FIG. 14A). Significant differences were found in gene expression (>1.5-fold change, p<0.05) in all examined compartments (FIG. 14B). In LT-HSC, 150 genes were differentially expressed (115 upregulated, 35 downregulated); in ST-HSC, 154 genes were differentially expressed (90 upregulated, 64 downregulated); and in GMP, 166 genes were differentially expressed (35 upregulated, 131 downregulated). Differentially expressed genes in each individual compartment (ΔLT-HSC, ΔST-HSC, ΔGMP) were then compared with each other to identify genes that were altered in all examined stem and progenitor compartments in AML patients. Using this intersection analysis, 11 genes were found that were consistently dysregulated in AML versus HC in all examined stem and progenitor compartments (FIG. 14B). To further characterize the cell populations used for gene expression comparison, fluorescence in-situ hybridization (FISH) was performed in sorted AML-LT-HSC and AML-ST-HSC. −7/7q− was present in the majority of cells (68% in LT-HSC (SD: 34%) and 92% in ST-HSC (SD: 10%)), indicating that these earliest definable cellular compartments were indeed part of the abnormal clone (data not shown; see (2)). Amongst the 11 intersecting genes, the interleukin 1 receptor accessory protein (IL1RAP) was consistently one of the most statistically significant differentially expressed genes in LT-HSC, ST-HSC, and GMP of AML patients with monosomy 7. Notably, when unfractionated blast cells of patients with −7/7q− AML were compared with healthy CD34+ cells, there was no difference in IL1RAP mRNA expression, suggesting that IL1RAP plays a role specifically in immature stem and progenitor cells. IL1RAP and RASGRP3 overexpression were confirmed, as well as NFIA downregulation in sorted LT-HSC, ST-HSC, and GMP by qRT-PCR on the same mRNA samples examined by microarray analysis, as well as samples of additional patients (N=2) (FIG. 14C; and data not shown; (2)).

IL1RAP Protein is Aberrantly Expressed on Stem and Progenitor Cells of AML Patients with −7/7q−.

Figures 15A, 15B, 15C, 15D, 15E:
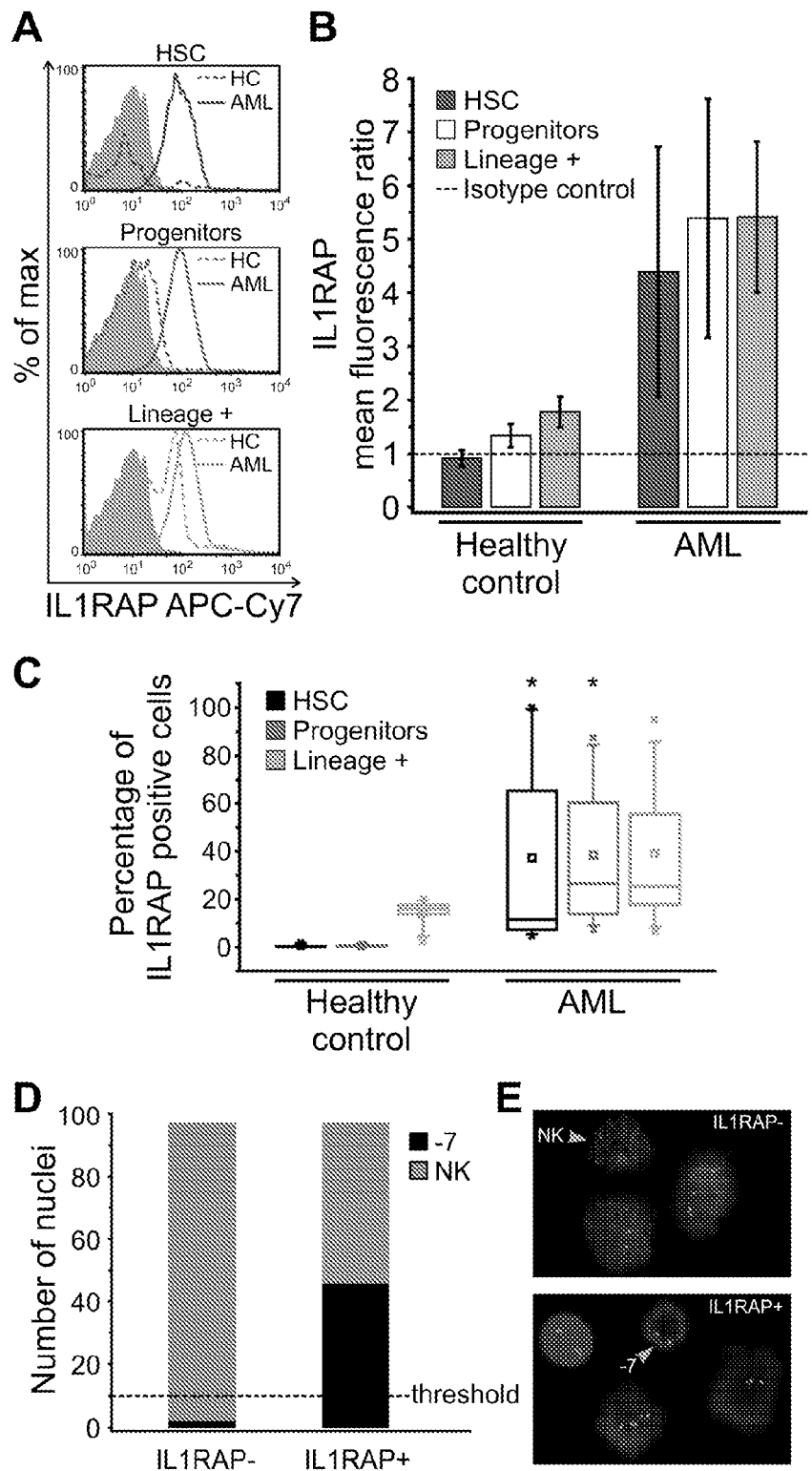
FIG. 15A-15E. IL1RAP protein is aberrantly expressed on distinct stem and progenitor cell compartments of AML patients with −7/7q−. Detection of IL1RAP expression at the protein level by flow cytometry in bone marrow-derived cells from healthy controls (n=5) and AML patients with −7/7q−(n=8). A) Representative histograms show the distribution of IL1RAP protein (cell surface) expression (fluorescence intensity) within phenotypically defined cell compartments of healthy control (HC; dotted line) and AML (solid line) samples measured using IL1RAP antibody coupled to APC-Cy7. Filled grey histograms correspond to the isotype control. B) Ratios of IL1RAP geometric mean fluorescence intensity relative to the isotype control (arbitrary unit (=1), indicated by the dotted line) for HSC in dark grey, progenitors in white, and lineage positive cells in light grey. Error bars indicate standard deviation. C) Box-and-whisker plots represent the percentage of IL1RAP positive cells in each cellular compartment, phenotypic HSC in black, progenitors in dark grey and lineage positive cells in light grey, in healthy control and AML bone marrow. An isotype control was used to define positive expression in each experiment. The central box represents the values from the 25th to 75th percentile. The middle square represents the mean and median is indicated by the horizontal line. A line extends from the minimum to the maximum value. Significant difference with healthy control counterparts is indicated with a black star. D) Fluorescence in-situ hybridization (FISH) of sorted IL1RAP-positive and IL1RAP-negative cells of an AML patient bearing monosomy 7 hybridized with the Vysis LSI D7S486 (7q31) SpectrumOrange/CEP 7 SpectrumGreen Probe. Bar graph shows the number of nuclei with normal karyotype (NK) and monosomy 7 (−7) for each group (N=100 nuclei analyzed per group; p<0.001 (Chi square)). The scoring threshold is indicated. E) Representative FISH image. The arrows indicate a normal karyotype (NK) FISH pattern with two individual green (centromere chromosome 7) and two orange (7q31) signals per nuclear section (top), and monosomy 7(−7) with one green and one orange signal (bottom), respectively.

To validate the finding of IL1RAP overexpression at the protein level, HSC and progenitors from AML patients with −7/7q− were stained with an IL1RAP-directed antibody, and IL1RAP expression was measured by flow cytometry. HSC and progenitors of AML patients expressed IL1RAP at the protein level, while HSC and progenitors from healthy controls did not show detectable IL1RAP surface protein expression (FIGS. 15A and 15B). The percentage of IL1RAP-expressing cells were determined within the subpopulations of HSC, progenitors, as well as lineage positive cells as a more mature cell population. While none of the healthy control HSC or progenitors contained significant numbers of IL1RAP+ cells, HSC and progenitors of AML patients displayed a highly significant percentage of IL1RAP-expressing cells (37.3%, p=0.006, and 38.5%, p=0.002, respectively) (FIG. 15C). In contrast, the lineage positive cell fraction of AML patients contained only moderately more IL1RAP-positive cells than healthy controls, and this difference was not significant (p=0.149) (FIG. 15C). To investigate whether aberrant IL1RAP expression is indeed a hallmark of immature cells which are part of the AML clone, IL1RAP+ and IL1RAP− cell fractions of a patient with monosomy 7 were sorted and FISH analysis was performed. Strikingly, 47% of the IL1RAP-positive cells harbored monosomy 7, while IL1RAP-negative cells did not show the cytogenetic aberration at all above threshold (FIGS. 15D and E). This indicates that the occurrence of the clonotypic −7/7q− aberration is indeed restricted to IL1RAP-expressing cells and that IL1RAP expression is a consistent feature of the cells which are part of the −7/7q− clone.

IL-1RAP is Overexpressed on Stem Cells in AML with Complex and Normal Karyotypes and in MDS.

Figure 5:
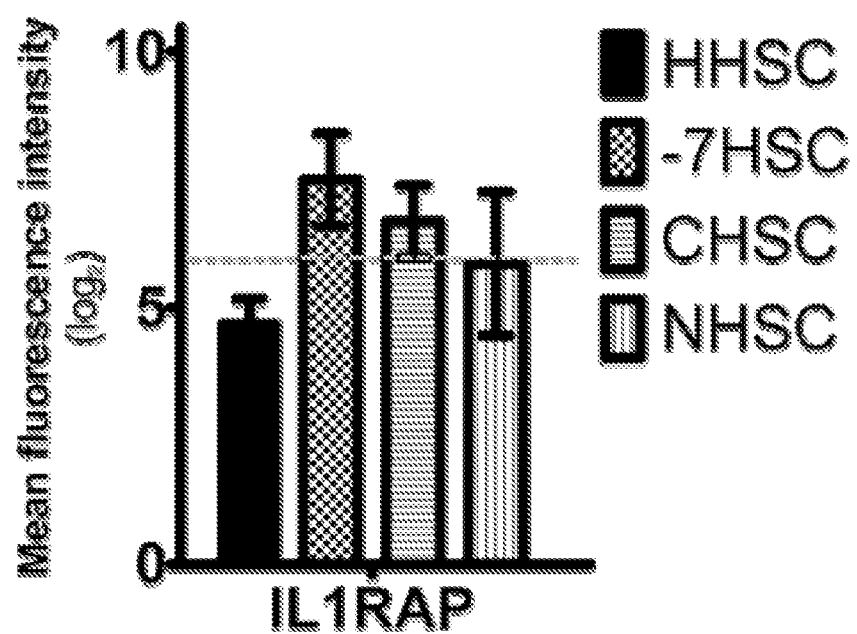
FIG. 5. IL1RAP is overexpressed in stem cells of AML patients with monosomy 7, complex, or normal karyotypes. HHSC, Healthy Control; −7HSC, Monosomy 7; CHSC, Complex Karyotype; NHSC, Normal Karyotype.
Figures 16A, 16B, 16C:
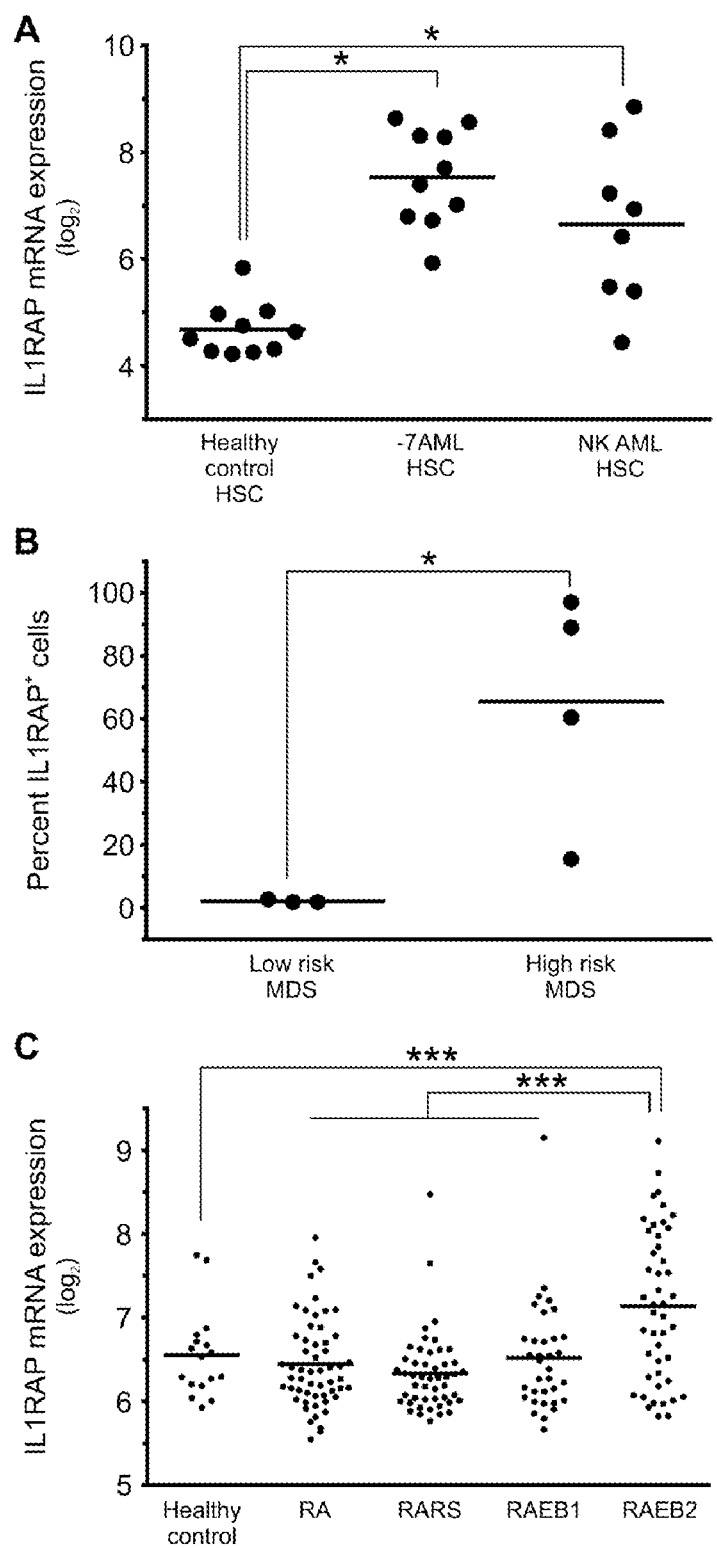
FIG. 16A-16C. IL1RAP is overexpressed on stem cells of patients with AML with monosomy 7, AML with normal karyotype, and high-risk MDS. A) IL1RAP gene expression in phenotypically defined HSC (Lin−CD34+CD38−) in healthy controls (N=10), AML with monosomy 7 (N=10) and AML with normal karyotype (N=8). Differences compared with the healthy control group are statistically significant with p<0.05 in both cases (*). B) IL1RAP protein expression was determined in Lin−CD34+CD38− cells in MDS patients (N=7; 3 with low risk, and 4 with high risk MDS). An isotype control was used to define IL1RAP positivity in each experiment. Percentages of IL1RAP+ cells are shown. Statistical significance is indicated (*p<0.05). C)

Overexpression of IL-1RAP was evaluated in other subtypes of leukemia. Primitive HSC and progenitor cells were isolated from human AML bone marrow extracts with normal and complex karyotypes by FACS and hybridized to gene expression arrays. mRNA levels of IL1RAP were upregulated in HSC and progenitors of some patients with complex and normal karyotypes when compared with healthy controls (FIGS. 5 and 16A). However, more inter-individual variation was observed in those disease subtypes. These data indicate that overexpression of IL1RAP is not restricted to monosomy 7 AML and might be part of a more general mechanism utilized for leukemia cell proliferation in various disease subtypes.

Myelodysplastic syndromes (MDS) are heterogeneous hematologic disorders that can progress to AML. Transformation to overt AML is particularly frequent in high risk MDS as defined by the new WHO classification (20, 21). To test whether IL1RAP plays a role in MDS, Lin−CD34+ CD38− HSC were sorted and analyzed from patients with MDS. High risk MDS patients displayed aberrant IL1RAP expression on their stem cells (average: 64%; range 17-97%), while stem cells of low risk MDS patients did not show a detectable fraction of IL1RAP-positive stem cells (FIG. 16B). When gene expression data from enriched CD34+ cells of a larger cohort of MDS patients (22) were analyzed, the subset of patients with RAEB-2 had significantly higher IL1RAP expression levels compared to patients with RA, RARS, and RAEB-1 ($p=4.23 \times 10^{-5}$), and in comparison to CD34+ cells from healthy controls ($p=7.4 \times 10^{-4}$) (FIG. 16C). These observations suggest that aberrant IL1RAP expression on stem cells discriminates high risk from low risk MDS and may thus be associated with inferior outcome.

Reduction of IL-1RAP Levels in AML Cell Lines Inhibits Proliferation.

Figure 6:
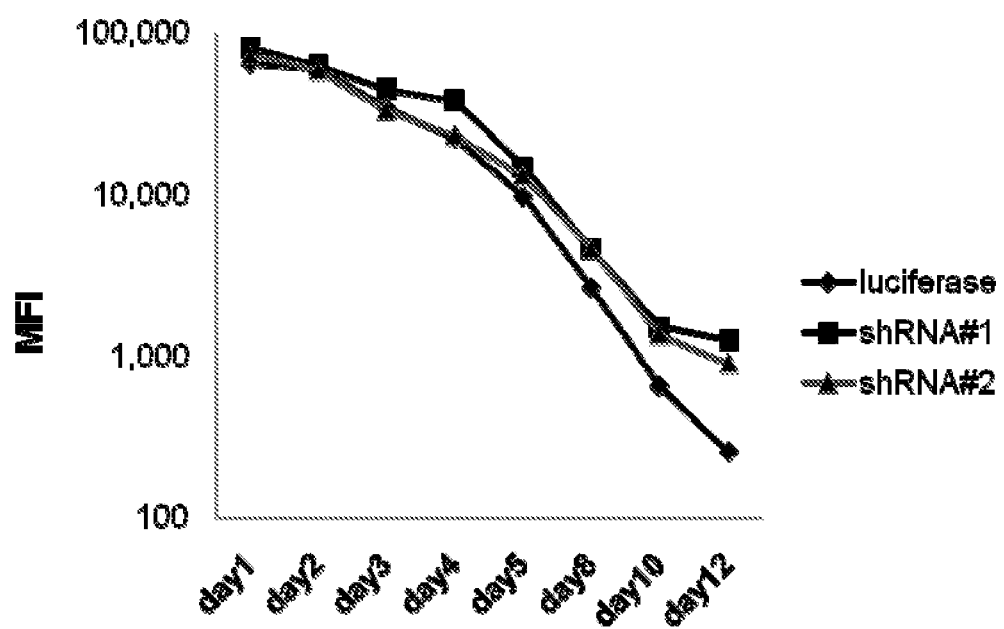
FIG. 6. Slower rate of cell division of AML cells upon reduction of IL1RAP expression. Cell tracker orange (CTO) label retention assay with THP-1 leukemia cells.
Figure 7:
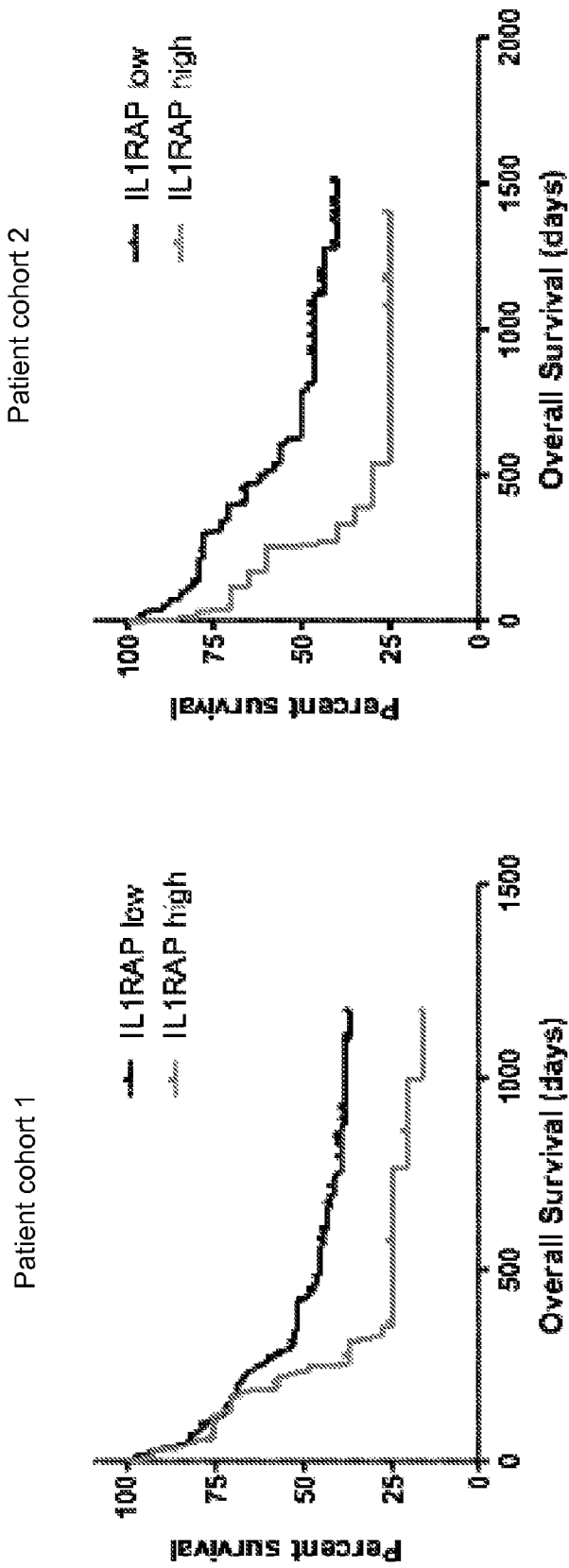
FIG. 7. Over-expression of IL-1RAP is clinically relevant. High IL-1RAP expression correlates with inferior survival of AML patients.

To investigate if the overexpression of IL1RAP is functionally relevant to AML cells, knockdown studies were performed using lentiviral shRNAs directed against IL1RAP. IL1RAP is an essential co-receptor for IL-1 signaling leading to a survival stimulus in other cell types. Therefore, it was hypothesized that its downregulation could have a specific impact on proliferation in AML cell lines. In fact, a significantly slower rate of cell division was found in AML cells upon IL-1RAP knock down (FIG. 6).

THP1 cells were transduced with these lentiviral shRNAs or with a non-silencing control, and subjected sorted GFP-positive, Annexin V-negative, DAPI-negative cells to clonogenic assays. Knockdown of IL1RAP led to a significant ($p<0.05$) 94% and 98% inhibition of leukemic colony formation of THP1 cells in comparison to the non-silencing control (FIG. 18A). Moreover, while the cell cycle state was not significantly affected, IL1RAP knockdown caused a significant increase of cellular death as determined by Annexin V/DAPI staining (FIG. 18B). Upon further examining AML cell lines, it was found that shRNA-mediated inhibition of IL1RAP reduced clonogenicity by 51.5% (shRNA#1) and 62% (shRNA#2) in OCI-AML3 cells ($p<0.05$), by 69% (shRNA#1) and 81% (shRNA#2) in HEL cells ($p<0.05$), and by 45% (shRNA#1) and 38.5% (shRNA#2) in HL-60 cells ($p<0.05$) (FIG. 18A).

The functional consequences of knockdown of IL1RAP in AML cells were also examined in an in vivo model. THP-1 cells treated with IL1RAP-directed shRNAs or control were injected into NOD-SCID-IL2 receptor-gamma-null recipient mice and mice were monitored and examined after 4 weeks. Mice transplanted with AML cells with IL1RAP knockdown showed drastically reduced morphological leukemic infiltration of their livers (FIG. 20). This finding was confirmed by FACS analysis for human CD15 in the liver, bone marrow, and spleen (FIG. 21). These results demonstrate that IL1RAP is functionally relevant in AML, and that reduction of IL1RAP leads to a decrease of the clonogenic capacity across different AML cell lines, and to AML inhibition in vivo. These findings indicate that targeting IL1RAP can be utilized as a therapeutic strategy for the inhibition of AML.

IL1RAP Overexpression is Independently Associated with Poor Clinical Outcome.

Phenotypic HSC in AML with normal karyotype showed substantial variability in the expression of IL1RAP (FIG. 16A). Some patients displayed IL1RAP levels as high as −7/7q− patients, while others had IL1RAP levels not distinguishable from healthy controls. An examination was performed as to whether IL1RAP expression levels were associated with known clinical or molecular parameters. For this purpose, an analysis was made of three large published datasets of patients with AML with normal karyotype, for which gene expression data of leukemic bulk (mononuclear) cells and time-to-event data were available (GSE10358, GSE12417 (U133A), GSE12417 (U133plus2)) (23, 24). As the top quartile of patients with normal karyotype had IL1RAP expression levels very similar to the ones observed in patients with −7/7q− (FIG. 16A), it was decided to use the 75th percentile to dichotomize patients with normal karyotype into "IL1RAP high" and "IL1RAP low" expressers. A comparison was made of the overall survival of AML patients with low versus high IL1RAP. In each of the three different data sets, high levels of IL1RAP expression were associated with inferior overall survival. Overall survival (irrespective of IL1RAP status) in all examined datasets was very similar, with superimposable survival curves, suggesting that the patient populations in these datasets and their clinical outcomes were comparable and could be combined for further analyses. Consistent with the analyses of the individual datasets, the evaluation of the combined set of AML patients with normal karyotype from the GSE10358 and GSE12417 (total N=317) confirmed that high IL1RAP levels were associated with inferior overall survival ($p=2.2 \times 10^{-7}$ (log-rank); hazard ratio (HR)=2.59 (95% confidence interval: 1.81 to 3.72); median survival: 7.82 months for IL1RAP high, 20 months for IL1RAP low; 5-yr survival rate: 11.3% for IL1RAP high, 33.1% for IL1RAP low) (FIG. 17). To assess whether the impact of IL1RAP expression on overall survival within AML with normal karyotype was independent of other prognostic factors, multivariate analysis was performed using a Cox regression model. In this analysis, high IL1RAP status remained an independent prognostic factor ($p=0.002$, HR=3.17 (95% confidence interval: 1.52 to 6.63)). Notably, in this analysis IL1RAP was an even stronger prognostic factor than FLT3 mutation status ($p=0.006$; HR=3.44 (95% confidence interval: 1.29 to 4.59)), which is a known independent covariate and used in the clinic for risk stratification of patients with normal karyotype.

Integration of Differential (Δ) Gene Expression Data of Different Purified Stem and Myeloid Progenitor Populations from Different Genetically Defined AML Subtypes.

In order to interrogate the data sets more comprehensively and exploit the particular strength of the simultaneous measurement of gene expression profiles from various stem and progenitor populations of individual patients, and of patients with different genetically defined subtypes of AML, the generated datasets were integrated. Specifically, intersections of differential gene expression were generated of 1) different stem and progenitor cells within distinct AML subtypes, and 2) LT-HSC, ST-HSC, GMP separately across different AML subtypes. The advantage of this approach is 2-fold. First, it allows for the first time the identification of novel candidate genes which are consistently deregulated at multiple immature stem and progenitor cell stages. Targeting these may be efficient at all relevant pre-leukemic cell stages including leukemia-cells-of origin. Second, the cross-comparison and intersection of deregulated transcription in stem cells across various well defined subtypes of leukemia reveals common aberrant gene expression which is likely to be functionally critical in stem cells of AML patients independent of the specific disease subtypes. Thus, these targets are expected to be particularly promising therapeutic targets.

Figure 12:
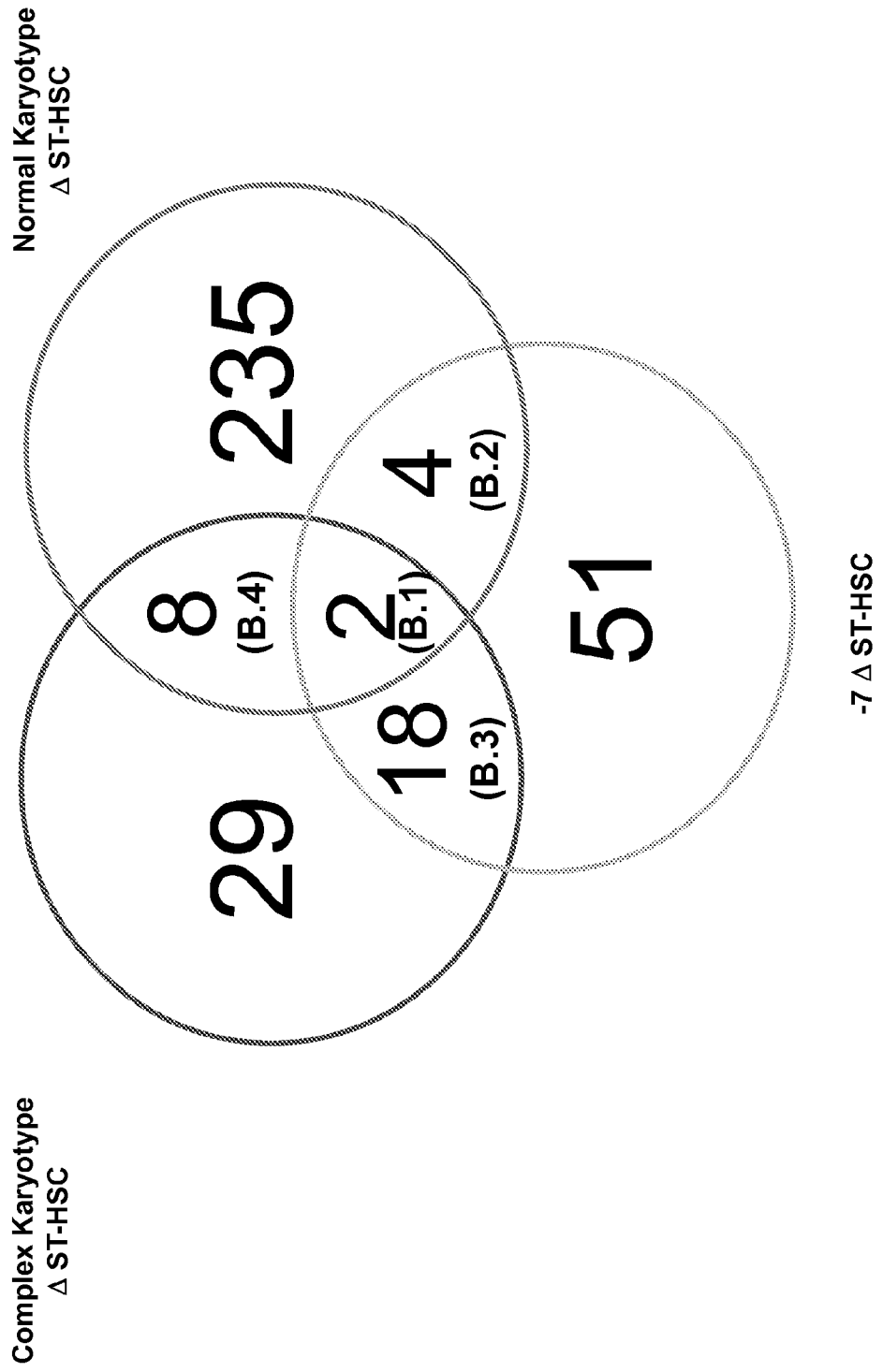
FIG. 12. Venn diagram of common deregulated gene expression in short-term hematopoietic stem cells in AML. Numbers in parentheses indicate that genes in areas of overlap are listed in Tables B.1-B.4.
Figure 13:
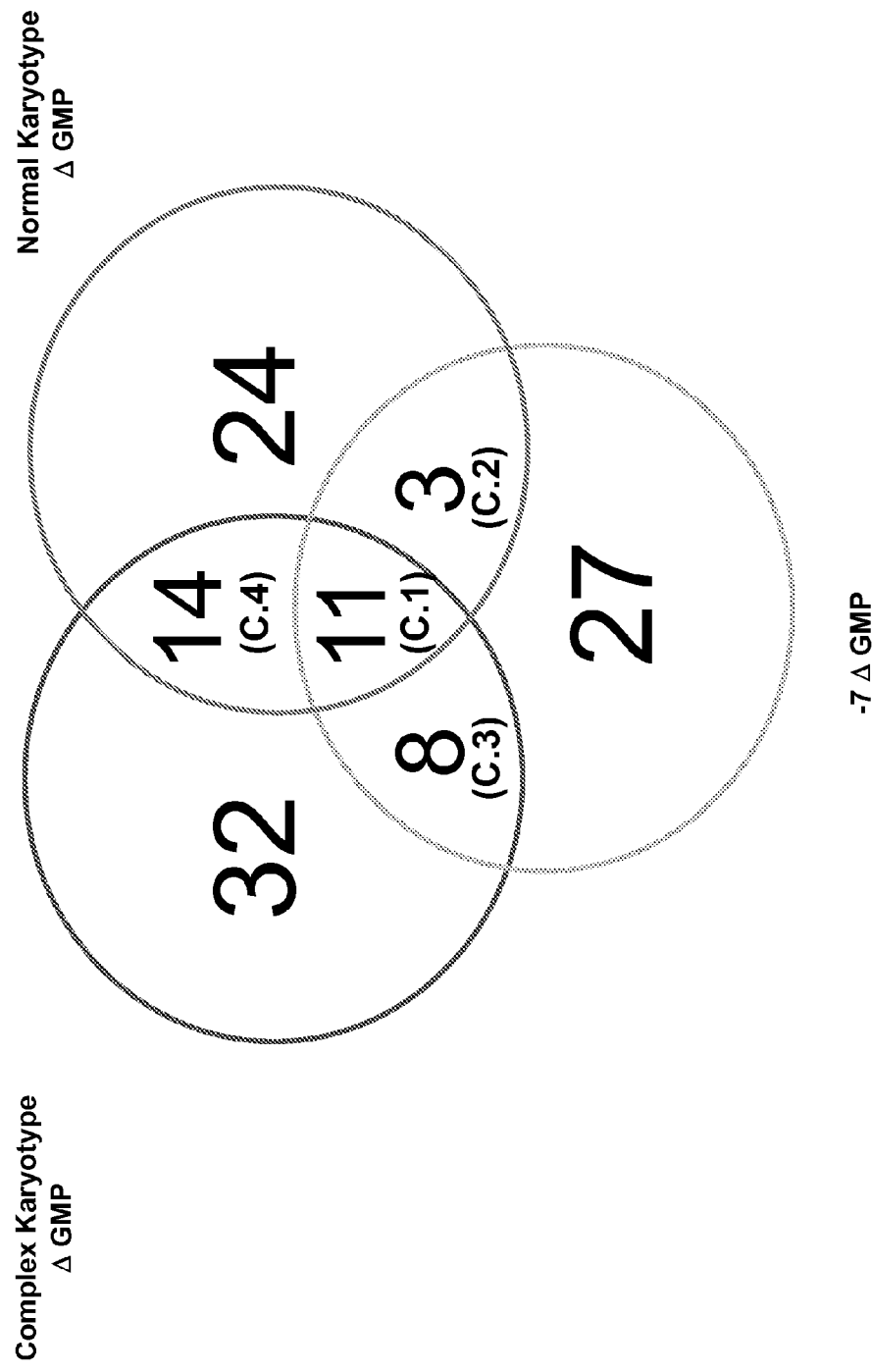
FIG. 13. Venn diagram of common deregulated gene expression in granulocytic-monocytic progenitors in AML. Numbers in parentheses indicate that genes in areas of overlap are listed in Tables C.1-C.4.

In detail, the following analyses of integrated gene expression data were carried out:

(ΔLT-HSC) vs (ΔST-HSC) vs (ΔGMP) within normal karyotype (NK) AML (FIG. 8), (ΔLT-HSC) vs (ΔST-HSC) vs (ΔGMP) within complex karyotype (CK) AML (FIG. 9), (ΔLT-HSC) vs (ΔST-HSC) vs (ΔGMP) within −7 AML (FIG. 10), ΔLT-HSC of (NK AML) vs (CK AML) vs (−7 AML) (FIG. 11), ΔST-HSC of (NK AML) vs (CK AML) vs (−7 AML) (FIG. 12), and ΔGMP of (NK AML) vs (CK AML) vs (−7 AML) (FIG. 13).

Figure 8:
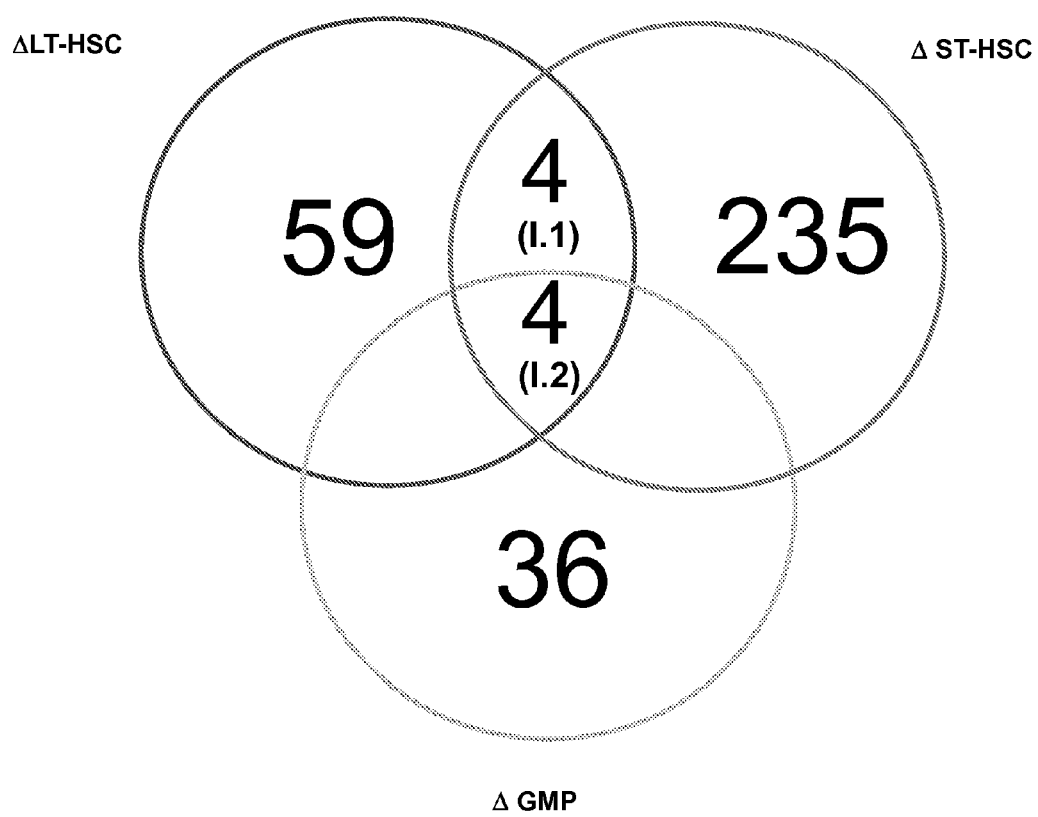
FIG. 8. Venn diagram of deregulated gene expression in normal karyotype AML. ΔLT-HSC and ΔST-HSC obtained using Lin−/CD34$^+$/CD38$^-$ cells; ΔGMP obtained using Lin−/CD34$^+$/CD38$^+$/CD123+/CD45RA+ cells. Numbers in parentheses indicate that genes in areas of overlap are listed in Tables 1.1 and 1.2.
Figure 9:
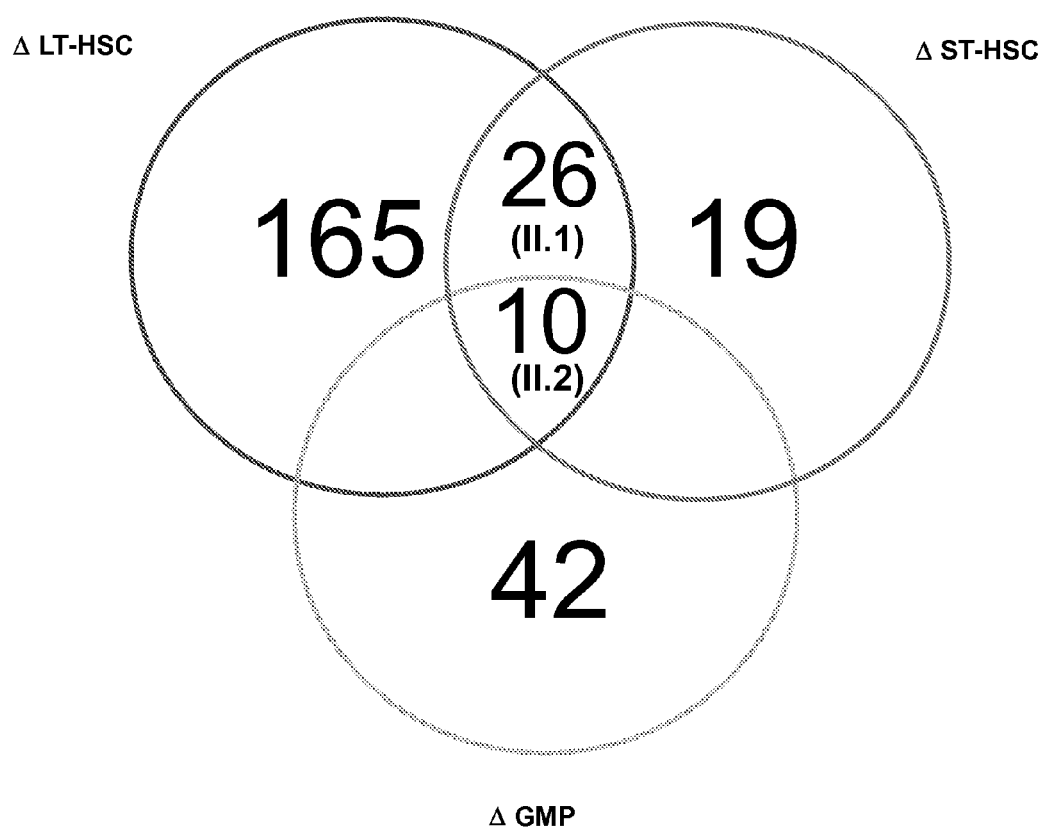
FIG. 9. Venn diagram of deregulated gene expression in complex karyotype AML. Numbers in parentheses indicate that genes in areas of overlap are listed in Tables II.1 and II.2.
Figure 10:
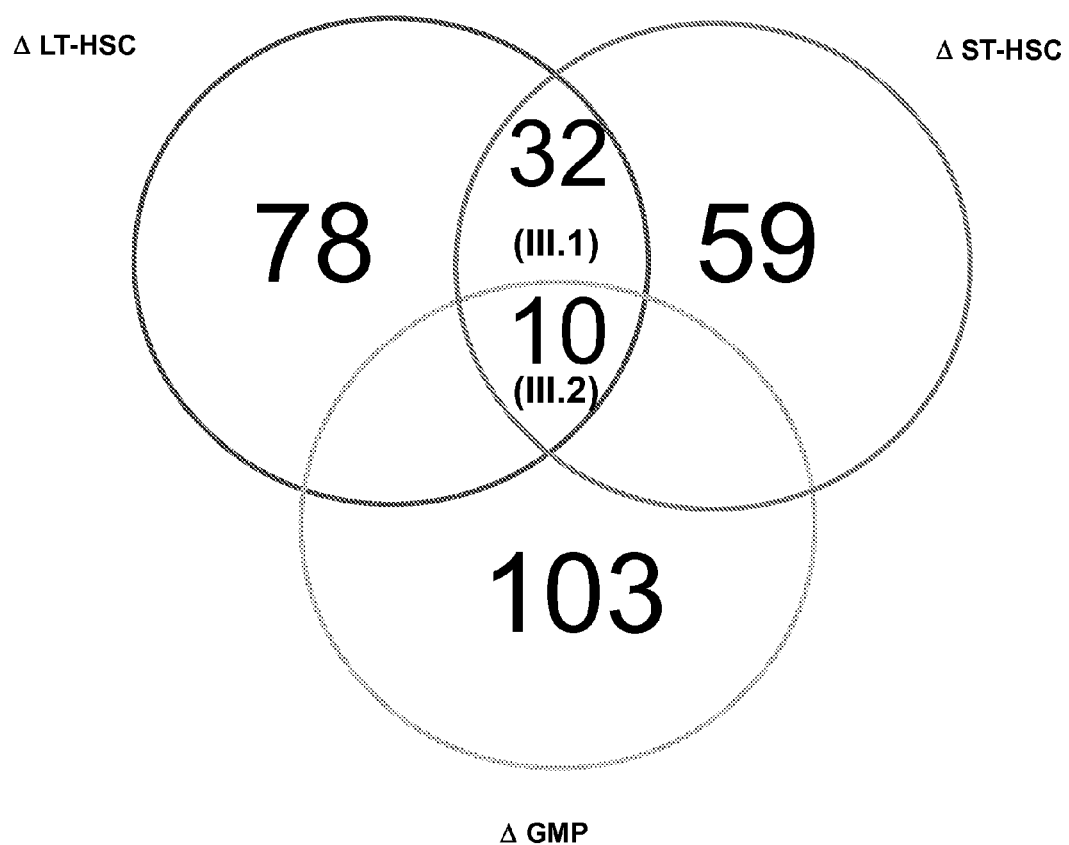
FIG. 10. Venn diagram of deregulated gene expression in −7 AML. Numbers in parentheses indicate that genes in areas of overlap are listed in Tables III.1 and III.2.
Figure 11:
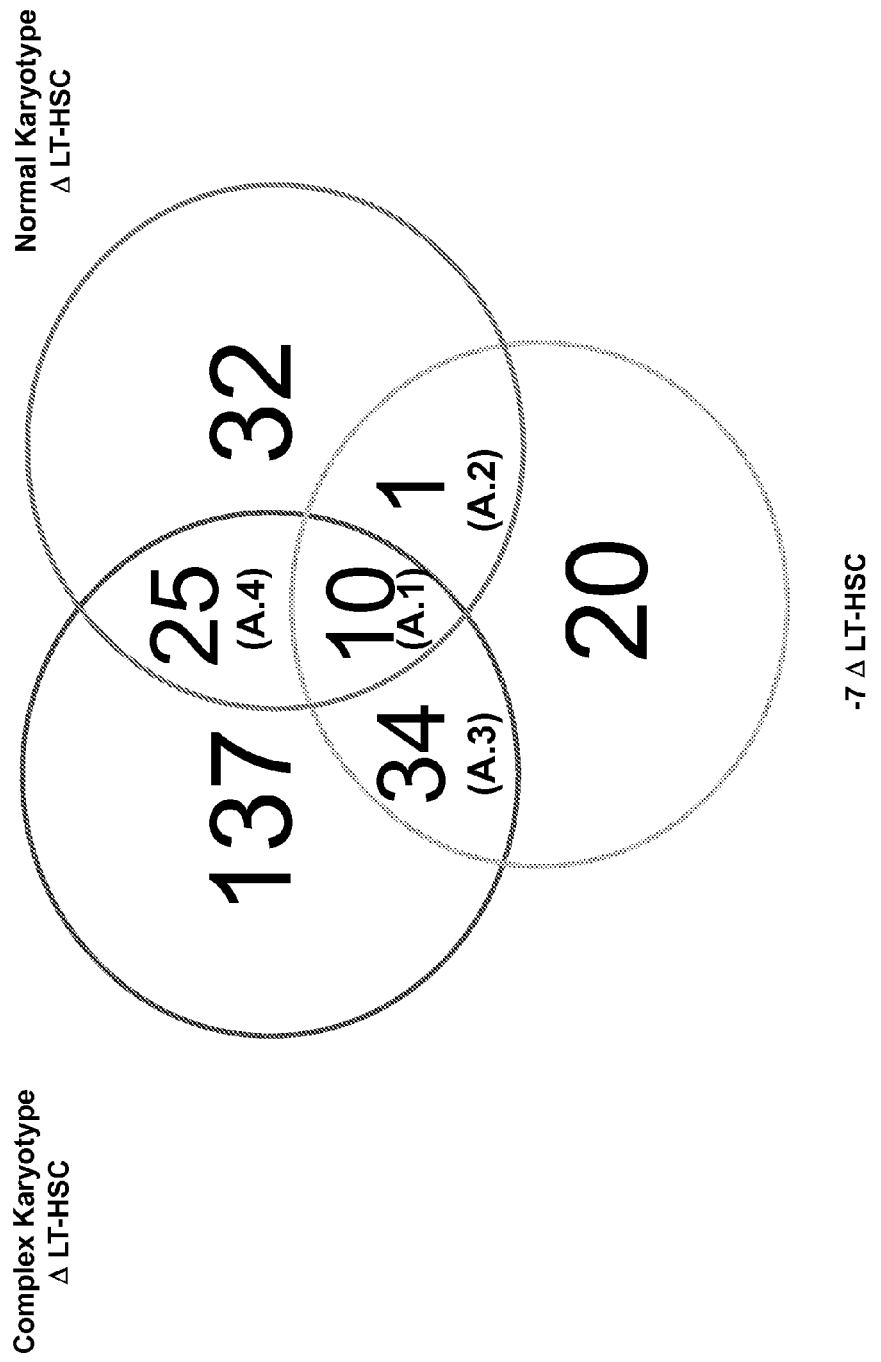
FIG. 11. Venn diagram of common deregulated gene expression in long-term hematopoietic stem cells in AML. Numbers in parentheses indicate that genes in areas of overlap are listed in Tables A.1-A.4.

This analysis focusing on genes commonly affected across different stem and progenitor populations or across different AML subtypes resulted in a number of novel and highly interesting gene targets. Detailed lists of genes resulting from each intersection are presented in Tables I.1 through C.4. Genes from the intersections shown in FIG. 8 are listed in Tables I.1 and I.2. Genes from the intersections shown in FIG. 9 are listed in Tables II.1 and II.2. Genes from the intersections shown in FIG. 10 are listed in Tables III.1 and III.2. Genes from the intersections shown in FIG. 11 are listed in Tables A.1-A.2. Genes from the intersections shown in FIG. 12 are listed in Tables B.1-B.4. Genes from the intersections shown in FIG. 13 are listed in Tables C.1-C.4.

TABLE I.1

Common deregulated genes in hematopoietic stem cells (ΔLT-HSC ∩ ΔST-HSC, excluding ΔGMP) in AML with normal karyotype.

| Accession | HUGO gene symbol | probe set ID 1.0ST | Fold Difference (log2[HHSC/NKHSC], 1.0ST) | p-value | Chromosome | Description |
|---|---|---|---|---|---|---|
| NM_006891 | CRYGD | 8058520 | −2.091 | 3.94E−07 | chr2 | crystallin, gamma D |
| NM_001964 | EGR1 | 8108370 | 2.773 | 1.53E−05 | chr5 | early growth response 1 |
| NR_002735 | SNORD61 | 8175432 | −4.785 | 3.04E−04 | chrX | small nucleolar RNA, C/D box 61 |
| NM_025190 | ANKRD36B | 8053834 | 2.352 | 1.07E−03 | chr2 | ankyrin repeat domain 36B |

TABLE I.2

Common deregulated genes in leukemic hematopoietic stem cells and progenitors (ΔLT-HSC ∩ ΔST-HSC ∩ ΔGMP) in AML with normal karyotype.

| Accession | HUGO gene symbol | probe set ID 1.0ST | Fold Difference (log2[H/NK], 1.0ST) | p-value | Chromosome | Description |
|---|---|---|---|---|---|---|
| NM_000584 | IL8 | 8095680 | 4.056 | 7.73E−08 | chr4 | interleukin 8 |
| NM_020529 | NFKBIA | 7978644 | 2.54 | 4.65E−06 | chr14 | nuclear factor of kappa light polypeptide gene enhancer in B-cells inhibitor, alpha |
| NM_014330 | PPP1R15A | 8030128 | 2.435 | 5.30E−05 | chr19 | protein phosphatase 1, regulatory (inhibitor) NM_001136529subunit 15A |
| NM_001136529 | SERPINE2 | 8059376 | −2.69 | 6.06E−05 | chr2 | serpin peptidase inhibitor, clade E (nexin, plasminogen activator inhibitor type 1), member 2 |

TABLE II.1

Common deregulated genes in hematopoietic stem cells (ΔLT-HSC ∩ ΔST-HSC, excluding ΔGMP) in AML with complex karyotype.

| Accession | HUGO gene symbol | probe set ID 1.0ST | Fold Difference (log2[HHSC/CKHSC], 1.0ST) | p-value | Chromosome | Description |
|---|---|---|---|---|---|---|
| NM_001098526 | AMICA1 | 7952022 | −3.215 | 1.21E−06 | chr11 | adhesion molecule, interacts with CXADR antigen 1 |
| NM_001150 | ANPEP | 7991335 | 2.803 | 1.77E−10 | chr15 | alanyl (membrane) aminopeptidase |
| NM_014059 | C13orf15 | 7968789 | 2.367 | 3.08E−05 | chr13 | chromosome 13 open reading frame 15 |
| NM_000186 | CFH | 7908459 | −4.169 | 2.18E−07 | chr1 | complement factor H |
| NM_001882 | CRHBP | 8106418 | −2.86 | 3.28E−05 | chr5 | corticotropin releasing hormone binding protein |
| NM_001964 | EGR1 | 8108370 | 2.413 | 1.58E−04 | chr5 | early growth response 1 |
| NM_052966 | FAM129A | 7922846 | 2.906 | 8.19E−05 | chr1 | family with sequence similarity 129, member A |
| NM_022763 | FNDC3B | 8083901 | 2.27 | 7.37E−05 | chr3 | fibronectin type III domain containing 3B |
| NM_001465 | FYB | 8111739 | 2.636 | 1.32E−03 | chr5 | FYN binding protein (FYB-120/130) |
| NM_020455 | GPR126 | 8122365 | −2.376 | 1.12E−04 | chr6 | G protein-coupled receptor 126 |
| NM_001945 | HBEGF | 8114572 | 2.14 | 5.49E−04 | chr5 | heparin-binding EGF-like growth factor |
| NM_002305 | LGALS1 | 8072876 | 2.809 | 5.91E−04 | chr22 | lectin, galactoside-binding, soluble, 1 |
| NM_130464 | LOC729978/NPIP | 8000636 | 4.066 | 2.21E−04 | chr16 | nuclear pore complex interacting protein-like 3 |
| AY699265 | mir-21 | 8008885 | 3.912 | 1.87E−05 | chr17 | microRNA21 |
| NM_002585 | PBX1 | 7906954 | −3.88 | 3.67E−08 | chr1 | pre-B-cell leukemia homeobox 1 |
| NM_000922 | PDE3B | 7938629 | 2.497 | 9.02E−08 | chr11 | phosphodiesterase 3B, cGMP-inhibited |
| NM_001134439 | PHLDB2 | 8081590 | −3.727 | 1.96E−04 | chr3 | pleckstrin homology-like domain, family B, member 2 |
| NM_024870 | PREX2 | 8146794 | −3.345 | 6.88E−07 | chr8 | phosphatidylinositol-3,4,5-trisphosphate-dependent Rac exchange factor 2 |
| NM_006259 | PRKG2 | 8101284 | −5.089 | 1.24E−05 | chr4 | protein kinase, cGMP-dependent, type II |
| NR_004378 | SNORD94 | 8043276 | −2.902 | 6.89E−05 | chr2 | small nucleolar RNA, C/D box 94 |
| NR_002574 | SNORD102 | 7968232 | −2.417 | 1.12E−06 | chr13 | small nucleolar RNA, C/D box 102 |
| NR_003320 | SNORD116-1 | 7981958 | −3.724 | 1.59E−06 | chr15 | *Homo sapiens* small nucleolar RNA, C/D box 116-5 (SNORD116-5), non-coding RNA. |
| NR_003319 | SNRPN | 7981955 | −2.709 | 4.04E−07 | chr15 | small nucleolar RNA, C/D box 116-4 |
| NM_001004470 | ST8SIA6 | 7932407 | −2.875 | 7.44E−07 | chr10 | ST8 alpha-N-acetyl-neuraminide alpha-2,8-sialyltransferase 6 |
| NM_005486 | TOM1L1 | 8008547 | −2.509 | 6.74E−05 | chr17 | target of myb1 (chicken)-like 1 |
| NM_004181 | UCHL1 | 8094778 | −2.19 | 6.31E−04 | chr4 | ubiquitin carboxyl-terminal esterase L1 (ubiquitin thiolesterase) |

TABLE II.2

Common deregulated genes in Hematopoietic stem and progenitor cells (ΔLT-HSC ∩ ΔST-HSC ∩ ΔGMP) in AML with complex karyotype.

| Accession | HUGO gene symbol | probe set ID 1.0ST | Fold Difference (log2[H/CK], 1.0ST) | p-value | Chromosome | Description |
|---|---|---|---|---|---|---|
| NM_000689 | ALDH1A1 | 8161755 | −2.713 | 9.00E−04 | chr9 | aldehyde dehydrogenase 1 family, member A1 |
| NM_078481 | CD97 | 8026300 | 2.87 | 3.39E−10 | chr19 | CD97 molecule |
| NM_144646 | IGJ | 8100827 | −3.687 | 6.85E−03 | chr4 | immunoglobulin J polypeptide, linker protein for immunoglobulin alpha and mu polypeptides |

TABLE II.2-continued

Common deregulated genes in Hematopoietic stem and progenitor cells
(ΔLT-HSC ∩ ΔST-HSC ∩ ΔGMP) in AML with complex karyotype.

| Accession | HUGO gene symbol | probe set ID 1.0ST | Fold Difference (log2[H/CK], 1.0ST) | p-value | Chromosome | Description |
|---|---|---|---|---|---|---|
| NM_000584 | IL8 | 8095680 | 3.245 | 4.26E−08 | chr4 | interleukin 8 |
| NM_001134673 | NFIA | 7901788 | −2.911 | 1.13E−05 | chr1 | nuclear factor I/A |
| NM_182943 | PLOD2 | 8091283 | −4.716 | 2.57E−08 | chr3 | procollagen-lysine, 2-oxoglutarate 5-dioxygenase 2 |
| NM_002351 | SH2D1A | 8169792 | 2.813 | 3.53E−05 | chrX | SH2 domain protein 1A |
| NR_002974 | SNORA42 | 7920873 | −2.62 | 1.07E−05 | chr1 | small nucleolar RNA, H/ACA box 42 |
| NR_000024 | SNORD46 | 7901048 | −3.702 | 1.02E−04 | chr1 | small nucleolar RNA, C/D box 46 |
| NR_000017 | SNORD36B | 8159006 | −3.294 | 3.02E−04 | chr9 | small nucleolar RNA, C/D box 36B |

TABLE III.1

Common deregulated genes in Hematopoietic Stem Cells
(ΔLT-HSC ∩ ΔST-HSC, excluding ΔGMP) in AML with monosomy 7.

| Accession | HUGO gene symbol | probe set ID 1.0ST | Fold Difference (log2[HHSC/−7HSC], 1.0ST) | p-value | Chromosome | Description |
|---|---|---|---|---|---|---|
| NM_025190 | ANKRD36B | 8053834 | 2.352 | 1.07E−03 | chr2 | ankyrin repeat domain 36B |
| NM_001150 | ANPEP | 7991335 | 2.803 | 1.77E−10 | chr15 | alanyl (membrane) aminopeptidase |
| NM_018429 | BDP1 | 8106025 | 2.253 | 0.034 | chr5 | B double prime 1, subunit of RNA polymerase III transcription initiation factor IIIB |
| NM_024913 | C7ORF58 | 8135734 | −2.236 | 2.24E−04 | chr7 | chromosome 7 open reading frame 58 |
| NM_005831 | CALCOCO2 | 8008113 | 1.98 | 1.64E−04 | Chr17 | Calcium binding and coiled-coil domain 2 |
| NM_001240 | CCNT1 | 7962831 | 2.585 | 0.018 | chr12 | cyclin T1 |
| NM_033646 | CDH7 | 8021668 | −2.321 | 6.91E−03 | chr18 | cadherin 7, type 2 |
| NM_000186 | CFH | 7908459 | −4.169 | 2.18E−07 | chr1 | complement factor H |
| NM_001831 | CLU | 8149927 | −2.333 | 4.98E−03 | chr8 | clusterin |
| NM_015904 | EIF5B | 8043861 | 3.155 | 7.83E−03 | chr2 | eukaryotic translation initiation factor 5B |
| NM_016242 | EMCN | 8101957 | −2.836 | 0.026 | chr4 | endomucin |
| NM_052966 | FAM129A | 7922846 | 2.906 | 8.19E−05 | chr1 | family with sequence similarity 129, member A |
| NM_178539 | FAM19A2 | 7964631 | −1.90 | 0.02 | chr12 | family with sequence similarity 19 (chemokine (C-C motif)-like), member A2 |
| NM_020455 | GPR126 | 8122365 | −2.376 | 1.12E−04 | chr6 | G protein-coupled receptor 126 |
| NM_002126 | HLF | 8008588 | −4.181 | 4.89E−05 | chr17 | hepatic leukemia factor |
| B012493 | KIAA1147 | 8143441 | −1.67 | 8.15E−3 | chr7 | predicted protein of HQ2561 |
| NM_002305 | LGALS1 | 8072876 | 2.809 | 5.91E−04 | chr22 | lectin, galactoside-binding, soluble, 1 |
| NM_012090 | MACF1 | 7900235 | 2.419 | 3.17E−05 | chr1 | microtubule-actin crosslinking factor 1 |
| NM_145686 | MAP4K4 | 8043945 | 1.88 | 0.04 | chr2 | mitogen-activated protein kinase kinasekinasekinase 4 |
| NM_015335 | MED13L | 7966706 | 2.55 | 0.011 | chr12 | mediator complex subunit 13-like |
| NM_005385 | NKTR | 8079079 | 2.134 | 2.10E−04 | chr3 | natural killer-tumor recognition sequence |
| NM_002610 | PDK1 | 8046408 | 2.486 | 3.09E−05 | chr2 | pyruvate dehydrogenase kinase, isozyme 1 |
| NM_020992 | PDLIM1 | 7935180 | 1.98 | 0.02 | chr10 | PDZ and LIM domain 1 |
| NM_001134439 | PHLDB2 | 8081590 | −4.171 | 6.26E−05 | chr3 | pleckstrin homology-like domain, family B, member 2 |
| NM_006259 | PRKG2 | 8101284 | −5.418 | 1.32E−07 | chr4 | protein kinase, cGMP-dependent, type II |
| NR_003003 | SCARNA17 | 8021183 | 2.519 | 1.63E−03 | chr18 | small Cajal body-specific RNA 17 |

TABLE III.1-continued

Common deregulated genes in Hematopoietic Stem Cells
(ΔLT-HSC ∩ ΔST-HSC, excluding ΔGMP) in AML with monosomy 7.

| Accession | HUGO gene symbol | probe set ID 1.0ST | Fold Difference (log2[HHSC/−7HSC], 1.0ST) | p-value | Chromosome | Description |
|---|---|---|---|---|---|---|
| NM_003005 | SELP | 7922200 | −2.524 | 1.52E−05 | chr1 | selectin P (granule membrane protein 140 kDa, antigen CD62) |
| NM_030674 | SLC38A1 | 7962516 | 2.221 | 5.55E−04 | chr12 | solute carrier family 38, member 1 |
| NM_016333 | SRRM2 | 7992692 | 1.66 | 8.78E−3 | chr16 | serine/arginine repetitive matrix 2 |
| NM_080390 | TCEAL2 | 8168892 | −2.038 | 0.042 | chrX | transcription elongation factor A (SII)-like 2 |
| NM_005486 | TOM1L1 | 8008547 | −1.97 | 0.03 | chr17 | target of myb1 (chicken)-like 1 |
| NM_004181 | UCHL1 | 8094778 | −2.178 | 5.62E−04 | chr4 | ubiquitin carboxyl-terminal esterase L1 (ubiquitin thiolesterase) |

TABLE III.2

Common deregulated genes in Hematopoietic Stem and Progenitor Cells
(ΔLT-HSC ∩ ΔST-HSC ∩ ΔGMP) in AML with monosomy 7.

| Accession | HUGO gene symbol | probe set ID 1.0ST | Fold Difference (log2[H/−7], 1.0ST) | p-value | Chromosome | Description |
|---|---|---|---|---|---|---|
| NM_001012978 | BEX5 | 8174141 | −2.739 | 0.000701 | chrX | brain expressed, X-linked 5 |
| NM_000875 | IGF1R | 7986383 | −2.249 | 2.62E−06 | chr15 | insulin-like growth factor 1 receptor |
| NM_000584 | IL8 | 8095680 | 2.583 | 6.53E−08 | chr4 | interleukin 8 |
| NM_002182 | IL1RAP | 8084794 | 2.464 | 0.000532 | chr3 | interleukin 1 receptor accessory protein |
| ENST00000326474 | LOC401097 | 8091735 | −4.244 | 1.27E−06 | chr3 | Similar to LOC166075 |
| NM_001137550 | LRRFIP1 | 8049542 | 2.018 | 0.015536 | chr2 | leucine rich repeat (in FLII) interacting protein 1 |
| AY699265 | mir-21 | 8008885 | 3.717 | 2.12E−05 | chr17 | microRNA 21 |
| NM_001134673 | NFIA | 7901788 | −2.350 | 5.64E−05 | chr1 | nuclear factor I/A |
| NM_170672 | RASGRP3 | 8041422 | 1.844 | 0.001014 | chr2 | RAS guanyl releasing protein 3 (calcium and DAG-regulated) |
| NR_027783 | SAT1 | 8166469 | 1.649 | 0.000146 | chrX | spermidine/spermine N1-acetyltransferase 1 |

TABLE A.1

Common deregulated gene expression in Long-Term Hematopoietic Stem cells (ΔLT-HSC)
in different AML subtypes (NK AML ∩ CK AML ∩ −7 AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_025190 | ANKRD36B | 8053834 | 2.994 | 0.044237 | chr2 | ankyrin repeat domain 36B |
| NM_018429 | BDP1 | 8177560 | 2.508 | 0.0099 | chr5 | B double prime 1, subunit of RNA polymerase III transcription initiation factor IIIB |
| NM_001135597 | CCDC88A | 8052269 | 2.740 | 0.011006 | chr2 | coiled-coil domain containing 88A |
| NM_001240 | CCNT1 | 7962831 | 2.581 | 0.001087 | chr12 | cyclin T1 |
| NM_015904 | EIF5B | 8043861 | 3.407 | 0.00019 | chr2 | eukaryotic translation initiation factor 5B |

TABLE A.1-continued

Common deregulated gene expression in Long-Term Hematopoietic Stem cells (ΔLT-HSC) in different AML subtypes (NK AML ∩ CK AML ∩ −7 AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_000317 | PTS | 7943882 | 2.116 | 6.33E−05 | chr11 | 6-pyruvoyltetrahydropterin synthase |
| NM_000584 | IL8 | 8095680 | 3.437 | 1.51E−05 | chr4 | interleukin 8 |
| NM_001137550 | LRRFIP1 | 8049542 | 3.570 | 0.000155 | chr2 | leucine rich repeat (in FLII) interacting protein 1 |
| NM_030674 | SLC38A1 | 7962516 | 3.203 | 0.005364 | chr12 | solute carrier family 38, member 1 |
| NM_080599 | UPF2 | 7932041 | 2.204 | 0.002112 | chr10 | UPF2 regulator of nonsense transcripts homolog (yeast) |

TABLE A.2

Common deregulated gene expression in Long-Term Hematopoietic Stem cells (ΔLT-HSC) in AML with normal karyotype and monosomy 7 (NK AML ∩ −7 AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_000712 | BLVRA | 8132515 | −2.06 | 2.54E−04 | chr7 | biliverdinreductase A |

TABLE A.3

Common deregulated gene expression in Long-Term Hematopoietic Stem cells (ΔLT-HSC) in AML with monosomy 7 and complex karyotype (CK AML ∩ −7 AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_001012978 | BEX5 | 8174141 | −2.047 | 0.001145 | chrX | brain expressed, X-linked 5 |
| AL133663 | C9orf102 | 8156601 | 1.995 | 0.00141 | chr9 | chromosome 9 open reading frame 102 |
| NM_033646 | CDH7 | 8021668 | −2.014 | 1.36E−05 | chr18 | cadherin 7, type 2 |
| NM_016343 | CENPF | 7909708 | 2.230 | 0.000106 | chr1 | centromere protein F, 350/400ka (mitosin) |
| NM_004762 | CYTH1 | 8018922 | 2.097 | 1.14E−05 | chr17 | cytohesin 1 |
| NM_001465 | FYB | 8111739 | 3.422 | 0.000118 | chr5 | FYN binding protein (FYB-120/130) |
| NM_020455 | GPR126 | 8122365 | −2.056 | 0.009304 | chr6 | G protein-coupled receptor 126 |
| NM_024567 | HMBOX1 | 8145636 | 2.671 | 6.29E−05 | chr8 | homeobox containing 1 |
| NM_002182 | IL1RAP | 8084794 | 2.363 | 1.74E−05 | chr3 | interleukin 1 receptor accessory protein |
| NM_002183 | IL3RA | 8165752 | 2.559 | 3.28E−05 | chrX | interleukin 3 receptor, alpha (low affinity) |
| NM_015434 | INTS7 | 7924119 | 1.713 | 0.001923 | chr1 | integrator complex subunit 7 |
| NM_012090 | MACF1 | 7900235 | 2.166 | 0.001021 | chr1 | microtubule-actin crosslinking factor 1 |
| NM_032485 | MCM8 | 8060813 | 2.032 | 0.00041 | chr20 | minichromosome maintenance complex component 8 |
| NM_015335 | MED13L | 7966706 | 2.363 | 0.000124 | chr12 | mediator complex subunit 13-like |
| AY699265 | mir-21 | 8008885 | 3.652 | 7.91E−06 | chr17 | microRNA 21 |
| NM_001134673 | NFIA | 7901788 | −2.598 | 0.000107 | chr1 | nuclear factor I/A |
| NM_006985 | NPIP | 7999766 | 1.970 | 0.005792 | chr16 | nuclear pore complex interacting protein |

TABLE A.3-continued

Common deregulated gene expression in Long-Term Hematopoietic Stem cells (ΔLT-HSC) in AML with monosomy 7 and complex karyotype (CK AML ∩ −7 AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_130464 | NPIPL3 | 8000636 | 3.657 | 0.022596 | chr16 | nuclear pore complex interacting protein-like 3 |
| NM_002610 | PDK1 | 8046408 | 1.504 | 0.000455 | chr2 | pyruvate dehydrogenase kinase, isozyme 1 |
| NM_001134439 | PHLDB2 | 8081590 | −3.916 | 1.5E−06 | chr3 | pleckstrin homology-like domain, family B, member 2 |
| NM_182734 | PLCB1 | 8060854 | 2.289 | 0.000217 | chr20 | phospholipase C, beta 1 (phosphoinositide-specific) |
| NM_006259 | PRKG2 | 8101284 | −4.312 | 3.19E−05 | chr4 | protein kinase, cGMP-dependent, type II |
| NR_003003 | SCARNA17 | 8021183 | 1.693 | 0.002577 | chr18 | small Cajal body-specific RNA 17 |
| NM_001142286 | SMC6 | 8050443 | 2.399 | 0.009314 | chr2 | structural maintenance of chromosomes 6/ |
| NM_015092 | SMG1 | 8002333 | 1.515 | 0.00726 | chr16 | SMG1 homolog, phosphatidylinositol 3-kinase-related kinase (*C. elegans*) |
| NR_002987 | SNHG12 | 7914212 | 3.086 | 3.8E−05 | chr1 | small nucleolar RNA, H/ACA box 61 |
| NR_002576 | SNORA21 | 8014755 | 2.122 | 0.001731 | chr17 | small nucleolar RNA, H/ACA box 21 |
| NR_002433 | SNORD12C | 8063345 | 2.697 | 0.002698 | chr20 | small nucleolar RNA, C/D box 12C |
| NM_032802 | SPPL2A | 7988753 | 2.619 | 0.001611 | chr15 | signal peptide peptidase-like 2A |
| NM_003234 | TFRC | 8093053 | 2.027 | 0.002593 | chr3 | transferrin receptor (p90, CD71) |
| NM_001080825 | TMEM120B | 7959312 | 1.956 | 0.000331 | chr12 | transmembrane protein 120B |
| NM_033285 | TP53INP1 | 8151890 | 2.238 | 7.05E−05 | chr8 | tumor protein p53 inducible nuclear protein 1 |
| NM_004181 | UCHL1 | 8094778 | −2.429 | 0.009195 | chr4 | ubiquitin carboxyl-terminal esterase L1 (ubiquitin thiolesterase) |
| NM_004666 | VNN1 | 8129618 | 2.914 | 0.000613 | chr6 | vanin 1 |

TABLE A.4

Common deregulated gene expression in Long-Term Hematopoietic Stem cells (ΔLT-HSC) in AML with normal and complex Karyotypes (NK AML ∩ CK AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_001995 | ACSL1 | 8103951 | 1.909 | 0.00246 | chr4 | acyl-CoA synthetase long-chain family member 1 |
| NM_014059 | C13orf15 | 7968789 | 1.793 | 0.007422 | chr13 | chromosome 13 open reading frame 15 |
| NR_027856 | CLK1 | 8058127 | 2.265 | 0.001263 | chr2 | CDC-like kinase 1 |
| NM_007207 | DUSP10 | 7924450 | 1.977 | 0.001416 | chr1 | dual specificity phosphatase 10 |
| NM_001964 | EGR1 | 8108370 | 2.426 | 0.003719 | chr5 | early growth response 1 |
| NM_001425 | EMP3 | 8030007 | 2.115 | 0.013962 | chr19 | epithelial membrane protein 3 |
| NM_018097 | HAUS2 | 7983123 | 2.239 | 1.66E−05 | chr15 | HAUS augmin-like complex, subunit 2 |
| NM_007040 | HNRNPUL1 | 8029029 | 1.946 | 0.001101 | chr19 | heterogeneous nuclear ribonucleoprotein U-like 1 |
| NM_001300 | KLF6 | 7931810 | 2.052 | 6.82E−05 | chr10 | Kruppel-like factor 6 |
| NM_182926 | KTN1 | 7974483 | 2.904 | 0.020218 | chr14 | kinectin 1 (kinesin receptor) |
| NM_020529 | NFKBIA | 7978644 | 2.742 | 0.000183 | chr14 | nuclear factor of kappa light polypeptide gene enhancer in B-cells inhibitor, alpha |

TABLE A.4-continued

Common deregulated gene expression in Long-Term Hematopoietic Stem cells (ΔLT-HSC) in AML with normal and complex Karyotypes (NK AML ∩ CK AML).

| Accession | HUGO gene symbol | probe set ID 1.0ST | Fold Difference (log2[HLT-HSC/ALT-HSC], 1.0ST) | p-value | Chromosome | Description |
|---|---|---|---|---|---|---|
| NM_172020 | POM121/POM121C | 8133326 | 2.274 | 0.015547 | chr7 | POM121 membrane glycoprotein (rat) |
| NM_014330 | PPP1R15A | 8030128 | 1.816 | 0.028292 | chr19 | protein phosphatase 1, regulatory (inhibitor) subunit 15A |
| NM_015172 | PRRC2C | 7907310 | 2.004 | 0.00011 | chr1 | BAT2 domain containing 1 |
| NM_006328 | RBM14 | 7941702 | 2.499 | 0.000194 | chr11 | RNA binding motif protein 14 |
| NR_002450 | RPL13 | 7997940 | −2.204 | 0.001229 | chr16 | small nucleolar RNA, C/D box 68 |
| NM_015138 | RTF1 | 7982904 | 1.908 | 0.034153 | chr15 | Rtf1, Paf1/RNA polymerase II complex component, homolog (S. cerevisiae) |
| NR_027783 | SAT1 | 8166469 | 2.549 | 6.44E−06 | chrX | spermidine/spermine N1-acetyltransferase 1 |
| NM_001136529 | SERPINE2 | 8059376 | −2.384 | 1.37E−05 | chr2 | serpin peptidase inhibitor, clade E (nexin, plasminogen activator inhibitor type 1), member 2 |
| NR_000006 | SNORD21 | 7903022 | −2.519 | 0.018022 | chr1 | small nucleolar RNA, C/D box 21 |
| NR_000024 | SNORD46 | 7901048 | −2.227 | 0.000627 | chr1 | small nucleolar RNA, C/D box 46 |
| NR_002735 | SNORD61 | 8175432 | −3.066 | 0.000208 | chrX | small nucleolar RNA, C/D box 61 |
| NR_002574 | SNORD102 | 7968232 | −1.601 | 0.000504 | chr13 | small nucleolar RNA, C/D box 102 |
| NR_003319 | SNRPN | 7981955 | −2.382 | 3.04E−05 | chr15 | small nucleolar RNA, C/D box 116-4 |
| NM_025160 | WDR26 | 7924582 | 2.101 | 0.001579 | chr1 | WD repeat domain 26 |

TABLE B.1

Common deregulated gene expression in Short-Term Hematopoietic Stem cells (ΔST-HSC) in different genetically defined AML subtypes (NK AML ∩ CK AML ∩ −7 AML).

| Accession | HUGO gene symbol | probe set ID 1.0ST | Fold Difference (log2[HST-HSC/AST-HSC], 1.0ST) | p-value | Chromosome | Description |
|---|---|---|---|---|---|---|
| NM_000584 | IL8 | 8095680 | 2.986 | 2.14E−07 | chr4 | interleukin 8 |
| NM_144646 | IGJ | 8100827 | −2.069 | 0.017522 | chr4 | immunoglobulin J polypeptide, linker protein for immunoglobulin alpha and mu polypeptides |

TABLE B.2

Common deregulated gene expression in Short-Term Hematopoietic Stem cells (ΔST-HSC) in AML with Normal Karyotype and monosomy 7 (NK AML ∩ −7 AML).

| Accession | HUGO gene symbol | probe set ID 1.0ST | Fold Difference (log2[HST-HSC/AST-HSC], 1.0ST) | p-value | Chromosome | Description |
|---|---|---|---|---|---|---|
| NM_025190 | ANKRD36B | 8053834 | 1.901 | 5.09E−06 | chr2 | ankyrin repeat domain 36B |
| NM_004088 | DNTT | 7929574 | −1.716 | 0.002869 | chr10 | deoxynucleotidyltransferase, terminal |

TABLE B.2-continued

Common deregulated gene expression in Short-Term Hematopoietic Stem cells (ΔST-HSC) in AML with Normal Karyotype and monosomy 7 (NK AML ∩ −7 AML).

| Accession | HUGO gene symbol | probe set ID 1.0ST | Fold Difference (log2[HST-HSC/AST-HSC], 1.0ST) | p-value | Chromosome | Description |
|---|---|---|---|---|---|---|
| NM_002166 | ID2 | 8040103 | 1.693 | 0.007561 | chr2 | inhibitor of DNA binding 2, dominant negative helix-loop-helix protein |
| NR_001296 | PRSS2 | 8136801 | −1.905 | 0.000218 | chr7 | trypsinogen C |

TABLE B.3

Common deregulated gene expression in Short-Term Hematopoietic Stem cells (ΔST-HSC) in AML with complex karyotype and monosomy 7 (CK AML ∩ −7 AML).

| Accession | HUGO gene symbol | probe set ID 1.0ST | Fold Difference (log2[HST-HSC/AST-HSC], 1.0ST) | p-value | Chromosome | Description |
|---|---|---|---|---|---|---|
| NM_001098526 | AMICA1 | 7952022 | −2.577 | 0.000108 | chr11 | adhesion molecule, interacts with CXADR antigen 1 |
| NM_024913 | C7ORF58 | 8135734 | −2.520 | 0.00021 | chr7 | chromosome 7 open reading frame 58 |
| NM_000186 | CFH | 7908459 | −3.594 | 2.34E−07 | chr1 | complement factor H |
| NM_001465 | FYB | 8111739 | 2.259 | 0.000519 | chr5 | FYN binding protein (FYB-120/130) |
| NM_020455 | GPR126 | 8122365 | −2.705 | 1.88E−06 | chr6 | G protein-coupled receptor 126 |
| NM_002305 | LGALS1 | 8072876 | 2.186 | 5.98E−05 | chr22 | lectin, galactoside-binding, soluble, 1 |
| AY699265 | mir-21 | 8008885 | 2.525 | 0.003805 | chr17 | microRNA 21 |
| NM_001134673 | NFIA | 7901788 | −2.678 | 3.72E−05 | chr1 | nuclear factor I/A |
| NM_006985 | NPIP | 7999766 | 1.964 | 1.19E−06 | chr16 | nuclear pore complex interacting protein |
| NM_130464 | NPIPL3 | 8000636 | 3.241 | 0.001264 | chr16 | nuclear pore complex interacting protein-like 3 |
| NM_018159 | NUDT11 | 8172708 | −2.432 | 5.58E−06 | chrX | nudix (nucleoside diphosphate linked moiety X)-type motif 11 |
| NM_002585 | PBX1 | 7906954 | −3.693 | 6.13E−09 | chr1 | pre-B-cell leukemia homeobox 1 |
| NM_000922 | PDE3B | 7938629 | 2.263 | 1.16E−06 | chr11 | phosphodiesterase 3B, cGMP-inhibited |
| NM_001134439 | PHLDB2 | 8081590 | −3.192 | 0.010542 | chr3 | pleckstrin homology-like domain, family B, member 2 |
| NM_182943 | PLOD2 | 8091283 | −4.190 | 9.07E−08 | chr3 | procollagen-lysine, 2-oxoglutarate 5-dioxygenase 2 |
| NM_024870 | PREX2 | 8146794 | −2.870 | 5.95E−05 | chr8 | phosphatidylinositol-3,4,5-trisphosphate-dependent Rac exchange factor 2 |
| NM_006259 | PRKG2 | 8101284 | −4.957 | 7.59E−09 | chr4 | protein kinase, cGMP-dependent, type II |
| NM_003005 | SELP | 7922200 | −2.214 | 4.11E−05 | chr1 | selectin P (granule membrane protein 140 kDa, antigen CD62) |

TABLE B.4

Common deregulated gene expression in Short-Term Hematopoietic Stem cells (ΔST-HSC)
in AML with Normal and complex karyotypes (NK AML ∩ CK AML).

| Accession | HUGO gene symbol | probe set ID 1.0ST | Fold Difference (log2[HST-HSC/AST-HSC], 1.0ST) | p-value | Chromosome | Description |
|---|---|---|---|---|---|---|
| NM_006891 | CRYGD | 8058520 | −2.326 | 6.51E−09 | chr2 | crystallin, gamma D |
| NM_001964 | EGR1 | 8108370 | 1.780 | 4.65E−05 | chr5 | early growth response 1 |
| NM_024930 | ELOVL7 | 8112274 | −3.103 | 2.59E−05 | chr5 | ELOVL family member 7, elongation of long chain fatty acids (yeast) |
| NM_032558 | HIATL1 | 8156538 | −1.908 | 0.0002 | chr9 | hippocampus abundant transcript-like 1 |
| NM_004897 | MINPP1 | 7928937 | −3.617 | 3.36E−07 | chr10 | multiple inositol polyphosphate histidine phosphatase, 1 |
| NM_003629 | PIK3R3 | 7915787 | −2.138 | 0.002696 | chr1 | phosphoinositide-3-kinase, regulatory subunit 3 (gamma) |
| NR_000017 | SNORD36B | 8159006 | −2.122 | 0.048712 | chr9 | small nucleolar RNA, C/D box 36B |
| NM_003407 | ZFP36 | 8028652 | 1.734 | 1.94E−06 | chr19 | zinc finger protein 36, C3H type, homolog (mouse) |

TABLE C.1

Common deregulated gene expression in Granulocyte-Monocyte Progenitors (ΔGMP) in
different genetically defined subtypes of AML (NK AML ∩ CK AML ∩ −7 AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NM_001738 | CA1 | 8151592 | −2.573 | 0.001739 | chr8 | carbonic anhydrase I |
| NM_002089 | CXCL2 | 8100994 | 2.977 | 5.36E−06 | chr4 | chemokine (C—X—C motif) ligand 2 |
| NM_001943 | DSG2 | 8020779 | −1.858 | 7.31E−05 | chr18 | desmoglein 2 |
| NM_000518 | HBB | 7946033 | −5.134 | 3.36E−08 | chr11 | hemoglobin, beta |
| NM_000584 | IL8 | 8095680 | 2.966 | 2.68E−07 | chr4 | interleukin 8 |
| NM_001137550 | LRRFIP1 | 8049540 | 2.233 | 0.00544 | chr2 | leucine rich repeat (in FLII) interacting protein 1 |
| NM_018159 | NUDT11 | 8172708 | −2.148 | 0.000417 | chrX | nudix (nucleoside diphosphate linked moiety X)-type motif 11 |
| NM_182943 | PLOD2 | 8091283 | −2.765 | 7.76E−08 | chr3 | procollagen-lysine, 2-oxoglutarate 5-dioxygenase 2 |
| NM_052969 | RPL39L | 8092654 | −3.235 | 7.52E−07 | chr3 | ribosomal protein L39-like |
| NM_001136529 | SERPINE2 | 8059376 | −2.762 | 1.16E−06 | chr2 | serpin peptidase inhibitor, clade E (nexin, plasminogen activator inhibitor type 1), member 2 |
| NM_004088 | DNTT | 7929574 | −3.356 | 2.53E−06 | chr10 | deoxynucleotidyltransferase, terminal |

TABLE C.2

Common deregulated gene expression in Granulocyte-Monocyte Progenitors (ΔGMP)
in AML with normal karyotype and monosomy 7 (NK AML ∩ −7 AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NM_013314 | BLNK | 7935270 | −2.110 | 0.000289 | chr10 | B-cell linker |
| NM_001559 | IL12RB2 | 7902205 | −1.913 | 0.000281 | chr1 | interleukin 12 receptor, beta 2 |

TABLE C.2-continued

Common deregulated gene expression in Granulocyte-Monocyte Progenitors (ΔGMP) in AML with normal karyotype and monosomy 7 (NK AML ∩ −7 AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NR_003001 | SCARNA7 | 8091778 | 1.767 | 0.001245 | chr3 | small Cajal body-specific RNA 7 |

TABLE C.3

Common deregulated gene expression in Granulocyte-Monocyte Progenitors (ΔGMP) in AML with complex karyotype and monosomy 7 (CK AML ∩ −7 AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NM_001254 | CDC6 | 8007071 | −1.937 | 0.000104 | chr17 | cell division cycle 6 homolog (S. cerevisiae) |
| NM_005192 | CDKN3 | 7974404 | −2.016 | 0.000156 | chr14 | cyclin-dependent kinase inhibitor 3 |
| NM_198947 | FAM111B | 7940147 | −1.987 | 0.015233 | chr11 | family with sequence similarity 111, member B |
| NM_144646 | IGJ | 8100827 | −3.556 | 2.89E−05 | chr4 | immunoglobulin J polypeptide, linker protein for immunoglobulin alpha and mu polypeptides |
| NM_001031716 | OBFC2A | 8047161 | 2.057 | 1.39E−05 | chr2 | oligonucleotide/oligosaccharide-binding fold containing 2A |
| NM_005024 | SERPINB10 | 8021645 | −2.887 | 1.88E−06 | chr18 | serpin peptidase inhibitor, clade B (ovalbumin), member 10 |
| NR_000007 | SNORD73A | 8097792 | 2.329 | 0.014153 | chr4 | small nucleolar RNA, C/D box 73A |
| NM_033512 | TSPYL5 | 8151931 | −1.944 | 0.006128 | chr8 | TSPY-like 5 |

TABLE C.4

Common deregulated gene expression in Granulocyte-Monocyte Progenitors (ΔGMP) in AML with complex and normal karyotypes (NK AML ∩ CK AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NM_000689 | ALDH1A1 | 8161755 | −2.308 | 0.000281 | chr9 | aldehyde dehydrogenase 1 family, member A1 |
| NM_001012978 | BEX5 | 8174141 | −2.069 | 7.86E−05 | chrX | brain expressed, X-linked 5 |
| NM_001251 | CD68 | 8004510 | 2.074 | 1.28E−06 | chr17 | CD68 molecule |
| NM_001781 | CD69 | 7961075 | 2.210 | 4.89E−07 | chr12 | CD69 molecule |
| NM_001432 | EREG | 8095728 | −2.128 | 0.004565 | chr4 | epiregulin |
| NM_000519 | HBD | 7946041 | −2.297 | 0.000122 | chr11 | hemoglobin, delta |
| NM_004897 | MINPP1 | 7928937 | −2.336 | 2.72E−05 | chr10 | multiple inositol polyphosphate histidine phosphatase, 1 |
| NM_001134673 | NFIA | 7901788 | −2.002 | 0.00089 | chr1 | nuclear factor I/A |
| NM_006186 | NR4A2 | 8055952 | 1.929 | 0.000856 | chr2 | nuclear receptor subfamily 4, group A, member 2 |
| NM_014879 | P2RY14 | 8091511 | −2.296 | 0.000179 | chr3 | purinergic receptor P2Y, G-protein coupled, 14 |
| NM_014330 | PPP1R15A | 8030128 | 1.820 | 2.46E−05 | chr19 | protein phosphatase 1, regulatory (inhibitor) subunit 15A |

TABLE C.4-continued

Common deregulated gene expression in Granulocyte-Monocyte Progenitors (ΔGMP) in AML with complex and normal karyotypes (NK AML ∩ CK AML).

| Accession | HUGO gene symbol | probe set ID 1.0ST | Fold Difference (log2[HGMP/AGMP], 1.0ST) | p-value | Chromosome | Description |
|---|---|---|---|---|---|---|
| NM_000963 | PTGS2 | 7922976 | 2.792 | 3.57E−06 | chr1 | prostaglandin-endoperoxide synthase 2 (prostaglandin G/H synthase and cyclooxygenase) |
| NM_002935 | RNASE3 | 7973105 | −1.834 | 0.000121 | chr14 | ribonuclease, RNase A family, 3 (eosinophil cationic protein) |
| NR_000017 | SNORD36B | 8159006 | −1.543 | 0.004295 | chr9 | small nucleolar RNA, C/D box 36B |

TABLE 4

IL1RAP mRNA expression is significantly higher in AML stem cells versus healthy control.

| Cell Population | Fold Change to Healthy Control | SD |
|---|---|---|
| LT-HSC | 6.5 | 1.07 |
| ST-HSC | 7.4 | 1.04 |
| GMP | 3.0 | 0.80 |

TABLE 5

IL1RAP protein expression on stem cells (CD34$^+$/CD38$^-$) of individual AML patients.

| | Specimen | Karotype | % IL1RAP$^+$ cells in CD34$^+$/CD38$^-$ population |
|---|---|---|---|
| AML | AML | 45, XX, −7[3]/46, XX[1] | 14.3 |
| | AML | 45, XY, −7[4]/45, XY, −7 del(12)[p11p13][16] | 11.7 |
| | AML | 46, XY,−7, +19[25] | 12.1 |
| | AML | 45, XX, −7[20] | 95.2 |
| | AML | 45, XX, −7[5]/46, XX[15](relapse) | 2.4 |
| | AML | | 54.3 |
| | AML | | 36.3 |
| Normal Bone Marrow | NBM-1 | NA | 2.4 |
| | NBM-2 | NA | 2.3 |
| | NBM-3 | NA | 0.3 |
| | NBM-4 | NA | 0.3 |
| | NBM-5 | NA | 0.1 |

TABLE 6

IL1RAP is overexpressed in stem and progenitor cells of patients with high risk myelodysplastic syndromes (MDS)

| Specimen | Diseases | % blasts | Karyotype | % IL1RAP$^+$ cells in CD34$^+$/CD38$^-$ population |
|---|---|---|---|---|
| MDS-1 | MDS (RAEB) | 10 | Normal | 89.1 |
| MDS-2 | MDS (RAEB) | 15 | del6, del7, del20, complex cyclogenetics | 14.1 |
| MDS-4 | MDS (RAEB) | 10-20 | 46, XY, del(7)(q21)[12]/48, XY, −7, +mar[8] | 80.0 |
| MDS-5 | MDS (RCMD) | 3 | del 13p | 0.2 |
| MDS-7 | MDS (RCMD) | <5 | complex, 43-45, XX, del(5)(q13q33), −7, del(10)(q24), add(12)(p11.2), −20cp20] | 1.1 |

TABLE 6-continued

IL1RAP is overexpressed in stem and progenitor cells of patients
with high risk myelodysplastic syndromes (MDS)

| Specimen | Diseases | % blasts | Karyotype | % IL1RAP+ cells in CD34+/CD38− population |
|---|---|---|---|---|
| MDS-8 | MDS (RCMD) | 2 | complex, 47, XY, del(5)(q13q33)×2, del(7)(q22), add(17)(p11.2)[cp14]/4BXY, t(3;14)(q21; q24), del(5)(q13q33), del(7)(q22), add(17)p11.2)del(20)(q11.2)[cp6] | 0.2 |

REFERENCES

1. Hanahan D, Weinberg R A: The hallmarks of cancer. Cell 2000, 100(1):57-70.
2. Barreyro L, Will B, Bartholdy B, Zhou L, Todorova T I, Stanley R F, Ben-Neriah S, Montagna C, Parekh S, Pellagatti A, Boultwood J, Paietta E, Ketterling R P, Cripe L, Fernandez H F, Greenberg P L, Tallman M S, Steidl C, Mitsiades C S, Verma A, Steidl U. Overexpression of interleukin 1 receptor accessory protein in stem and progenitor cells and outcome correlation in AML and MDS. Blood. 2012 Jun. 21. [Epub ahead of print].
3. Wang J C, Dick J E: Cancer stem cells: lessons from leukemia. Trends Cell Biol 2005, 15(9):494-501.
4. Jordan C T, Guzman M L, Noble M: Cancer stem cells. N Engl J Med 2006, 355(12):1253-1261.
5. Visvader J E: Cells of origin in cancer. Nature 2011, 469(7330):314-322.
6. Tenen D G: Disruption of differentiation in human cancer: AML shows the way. Nat Rev Cancer 2003, 3(2):89-101.
7. Steidl U, Rosenbauer F, Verhaak R G, Gu X, Ebralidze A, Otu H H, Klippel S, Steidl C, Bruns I, Costa D B, Wagner K, Aivado M, Kobbe G, Valk P J, Passegue E, Libermann T A, Delwel R, Tenen D G: Essential role of Jun family transcription factors in PU.1 knockdown-induced leukemic stem cells. Nat Genet 2006, 38(11):1269-1277.
8. Steidl U, Steidl C, Ebralidze A, Chapuy B, Han H J, Will B, Rosenbauer F, Becker A, Wagner K, Koschmieder S, Kobayashi S, Costa D B, Schulz T, O'Brien K B, Verhaak R G, Delwel R, Haase D, Trumper L, Krauter J, Kohwi-Shigematsu T, Griesinger F, Tenen D G: A distal single nucleotide polymorphism alters long-range regulation of the PU.1 gene in acute myeloid leukemia. J Clin Invest 2007, 117(9):2611-2620.
9. Will B, Steidl U: Multi-parameter fluorescence-activated cell sorting and analysis of stem and progenitor cells in myeloid malignancies. Best Pract Res Clin Haematol 2010, 23(3):391-401.
10. Haase D, Feuring-Buske M, Konemann S, Fonatsch C, Troff C, Verbeek W, Pekrun A, Hiddemann W, Wormann B: Evidence for malignant transformation in acute myeloid leukemia at the level of early hematopoietic stem cells by cytogenetic analysis of CD34+ subpopulations. Blood 1995, 86(8):2906-2912.
11. Mehrotra B, George T I, Kavanau K, Avet-Loiseau H, Moore D, 2nd, Willman C L, Slovak M L, Atwater S, Head D R, Pallavicini M G: Cytogenetically aberrant cells in the stem cell compartment (CD34+lin−) in acute myeloid leukemia. Blood 1995, 86(3):1139-1147.
12. Nilsson L, Astrand-Grundstrom I, Anderson K, Arvidsson I, Hokland P, Bryder D, Kjeldsen L, Johansson B, Hellstrom-Lindberg E, Hast R, Jacobsen S E: Involvement and functional impairment of the CD34(+)CD38(−) Thy-1(+) hematopoietic stem cell pool in myelodysplastic syndromes with trisomy 8. Blood 2002, 100(1):259-267.
13. Nilsson L, Astrand-Grundstrom I, Arvidsson I, Jacobsson B, Hellstrom-Lindberg E, Hast R, Jacobsen S E: Isolation and characterization of hematopoietic progenitor/stem cells in 5q-deleted myelodysplastic syndromes: evidence for involvement at the hematopoietic stem cell level. Blood 2000, 96(6):2012-2021.
14. Nilsson L, Eden P, Olsson E, Mansson R, Astrand-Grundstrom I, Strombeck B, Theilgaard-Monch K, Anderson K, Hast R, Hellstrom-Lindberg E, Samuelsson J, Bergh G, Nerlov C, Johansson B, Sigvardsson M, Borg A, Jacobsen S E: The molecular signature of MDS stem cells supports a stem-cell origin of 5q myelodysplastic syndromes. Blood 2007, 110(8):3005-3014.
15. WO 2011/021014 A2, published Feb. 24, 2011, Cantargia A B, Novel Agents and Uses Thereof.
16. Järås M, Johnels P, Hansen N, et al. Isolation and killing of candidate chronic myeloid leukemia stem cells by antibody targeting of IL-1 receptor accessory protein. Proc Natl Acad Sci USA. 2010; 107(37): 16280-16285.
17. Pellagatti A, Cazzola M, Giagounidis A, et al. Deregulated gene expression pathways in myelodysplastic syndrome hematopoietic stem cells. Leukemia. 2010; 24(4): 756-764.
18. Manz M G, Miyamoto T, Akashi K, Weissman I L. Prospective isolation of human clonogenic common myeloid progenitors. Proceedings of the National Academy of Sciences of the United States of America. 2002; 99(18):11872-11877.
19. Jamieson C H, Ailles L E, Dylla S J, et al. Granulocyte-macrophage progenitors as candidate leukemic stem cells in blast-crisis CML. N Engl J Med. 2004; 351(7):657-667.
20. Vardiman J W, Harris N L, Brunning R D. The World Health Organization (WHO) classification of the myeloid neoplasms. Blood. 2002; 100(7):2292-2302.
21. Vardiman J W, Thiele J, Arber D A, et al. The 2008 revision of the World Health Organization (WHO) classification of myeloid neoplasms and acute leukemia: rationale and important changes. Blood. 2009; 114(5): 937-951.
22. Pellagatti A, Cazzola M, Giagounidis A, et al. Deregulated gene expression pathways in myelodysplastic syndrome hematopoietic stem cells. Leukemia. 2010; 24(4): 756-764.
23. Metzeler K H, Hummel M, Bloomfield C D, et al. An 86-probe-set gene-expression signature predicts survival in cytogenetically normal acute myeloid leukemia. Blood. 2008; 112(10):4193-4201.
24. Tomasson M H, Xiang Z, Walgren R, et al. Somatic mutations and germline sequence variants in the expressed tyrosine kinase genes of patients with de novo acute myeloid leukemia. Blood. 2008; 111(9):4797-4808.

What is claimed is:

1. A method for treating a subject having acute myeloid leukemia (AML) or a myelodysplastic syndrome (MDS) comprising administering to the subject an antibody to interleukin 8 (IL8) in an amount effective to treat AML or MDS in a subject.

2. The method of claim 1, wherein prior to administering the antibody to the subject, the subject is tested for overexpression of IL8 in early stem or progenitor cells, compared to the level of expression of IL8 in a control population without AML or a myelodysplastic syndrome (MDS).

3. The method of claim 2, wherein IL8 mRNA expression is tested.

4. The method of claim 2, wherein IL8 protein expression is tested.

5. The method of claim 1, wherein the antibody decreases the activity of IL8.

6. The method of claim 1, wherein the antibody is conjugated to a cytotoxic agent.

7. The method of claim 6, wherein the cytotoxic agent is a radioisotope or chemotherapeutic agent.

8. The method of claim 1, wherein the antibody elicits an immune response.

9. The method of claim 1, wherein the antibody inhibits division of AML, cells.

10. The method of claim 1, wherein the antibody affects AML/MDS stem cells.

\* \* \* \* \*